United States Patent [19]

El Ahmad et al.

[11] Patent Number: 5,846,980

[45] Date of Patent: Dec. 8, 1998

[54] N-(BENZHYDRYLOXYALKYL)-4-(CARBOXY/ CARBAMOYL METHYL)-PIPERIDINE DERIVATIVES AS ANTIDEPRESSANTS

[75] Inventors: Youssef El Ahmad, Le Mee sur Seine; Pierre-Yves Fiez-Vandal, Avon; Elisabeth Laurent; Philippe Maillet, both of Paris; Roland Ollivier, Fontainebleau, all of France

[73] Assignee: Cooperation Pharmaceutique Francaise, Melun, France

[21] Appl. No.: 704,755

[22] PCT Filed: Mar. 24, 1995

[86] PCT No.: PCT/FR95/00367

§ 371 Date: Oct. 16, 1996

§ 102(e) Date: Oct. 16, 1996

[87] PCT Pub. No.: WO95/26336

PCT Pub. Date: Oct. 5, 1995

[30] Foreign Application Priority Data

Mar. 25, 1994 [FR] France ................................ 94 03562

[51] Int. Cl.⁶ ................... A61K 31/445; C07D 211/34; C07D 211/70
[52] U.S. Cl. ................... 514/317; 514/315; 514/428; 546/236; 548/428
[58] Field of Search ................... 546/236; 548/574; 514/315, 317, 428

[56] References Cited

U.S. PATENT DOCUMENTS 4,983,614  1/1991  Bizas .................................. 514/317
5,053,521 10/1991  Pavia ................................. 548/572
5,294,623  3/1994  Fukumi ............................. 514/317

OTHER PUBLICATIONS

Pavia et al. "Structure Activity studies on benzhydrol containing nipecotic acid . . . " J. Med. Chem. v.35, pp. 4238–4248, 1992.

Fumuki et al. "Preparation of antiallergic . . . " CA 114:42585, 1991.

*Primary Examiner*—Ceila Chang
*Attorney, Agent, or Firm*—Dennison, Meserole, Pollack & Scheiner

[57] ABSTRACT

The invention relates to substituted nitrogenous heterocycles derivatives of general formula (I)

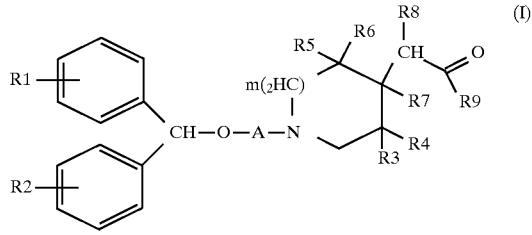

in the racemic or optically pure form and/or in the form of cis/trans isomers, their pharmaceutically acceptable salts, and their use for preparing drugs having psychrotropic activity, especially antidepressant activity.

14 Claims, No Drawings

N-(BENZHYDRYLOXYALKYL)-4-(CARBOXY/CARBAMOYL METHYL)-PIPERIDINE DERIVATIVES AS ANTIDEPRESSANTS

The subject of the invention is new substituted nitrogenous heterocycle derivatives, their preparation and their biological and pharmaceutical applications.

The invention is more particularly targeted at substituted nitrogenous heterocycle derivatives, their isomers and their metabolites having a therapeutic activity, in particular a psychotropic activity and more especially an antidepressant activity.

Aryl-1,4-dialk(en)ylpiperazines (Eur. J. Med. Chem. 15, 363–370, 1980) are selective and powerful inhibitors of dopamine re-uptake, they exhibit a nanomolar affinity for this re-uptake site and also bind to the carrier for this amine (Neurochem. int. 15, 3, 325–332, 1989; Eur. J. Pharmacol. 177, 91–94, 1990) and are potential antidepressants.

(1-[2-(Diphenylmethoxy)ethyl]-4-(3-phenylpropenyl) piperazine (Psychopharmacol., 101, 344–353, 1990) decreases the sleep induced by phenobarbital, increases the motor activity of the animals, induces stereotypic behaviors and decreases the immobility time of the mouse in the Porsolt behavioral despair test (Arch. Intern. Pharmacodyn. Therap., 225, 327, 1977) but antagonizes neither the ptosis nor the hypothermia induced by reserpine, nor the hypothermia induced by apomorphine. The behavioral despair test is the only predictive test for antidepressant activity with respect to which this product is active; however, the effect on the immobility time occurs at doses which cause an increase in the spontaneous motility of the animals, which is regarded as a bias and does not enable it to be irrefutably concluded that an antidepressant-type activity exists.

Selective or non-selective inhibitors of dopamine re-uptake are also active with respect to certain predictive tests for an activity in the treatment of Parkinson's disease (Psychopharmacol. Berl., 153–164–195; Psychopharmacol., 101, 344–195; Psychopharmacol., 101, 344–353, 1990).

1-[1-(2-Benzo[b]thiophenyl)cyclohexyl]piperidine and 1,2,3,4-tetrahydro-2-methyl-4-phenyl-8-isoquinolinamine inhibit dopamine and noradrenaline re-uptake (Drugs, 18, 1–24, 1979; Psychopharmacol., 101, 344–353, 1990). These two products decrease the immobility time of the mouse in the behavioral despair test; they also antagonize the ptosis and the hypothermia induced by reserpine and the hypothermia caused by apomorphine. The responses observed with respect to these pharmacological tests are predictive of an antidepressant activity; moreover, this effect is demonstrated in human clinical studies for 1,2,3,4-tetrahydro-2-methyl-4-phenyl-8-isoquinolinamine.

The studies carried out have made it possible to develop a family of substituted nitrogenous heterocycle derivatives endowed with inhibiting properties for dopamine, noradrenaline and serotonin re-uptake exhibiting, at low doses, the desired properties with respect to pharmacological tests predictive of an antidepressant activity.

The subject of the present invention is the use of the compounds of formula (I), which are substituted nitrogenous heterocycle derivatives, for the preparation of medicaments possessing psychotropic activity, in particular antidepressant activity,

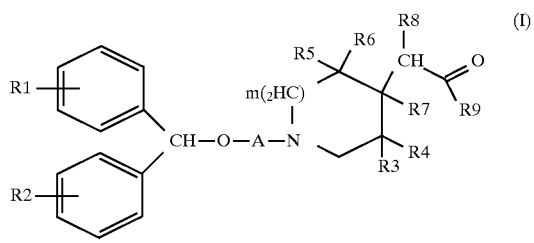

in which:
$R^1$ and $R^2$, which are identical or different, represent a hydrogen atom, a halogen atom, a $C_1$–$C_6$ alkyl group, a $C_2$–$C_6$ alkoxy group or a trifluoromethyl group,
m is an integer between 0 and 2,
A is a $C_2$–$C_8$ alkylene chain or a $C_2$–$C_8$ alkenylene chain,
the heterocyclic unit of general formula Q:

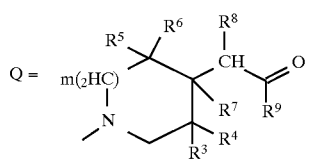

in which
$R^9$ represents
a unit —$OZ_1$ in which $Z_1$ represents hydrogen, a $C_1$–$C_{12}$ alkyl, a $C_3$–$C_7$ cycloalkyl, a $C_1$–$C_{12}$ alkyl which is substituted by one or a number of optionally esterified alcohol functional groups or a $C_1$–$C_{12}$ alkyl substituted by an —N(RaRb) group in which Ra and Rb, independently of one another, represent hydrogen or a $C_1$–$C_4$ alkyl group or alternatively Ra and Rb, together with the nitrogen atom to wich they are bonded, form a 5- to 7-membered heterocycle optionally containing a second heteroatom,
a unit —OM in which M is an alkali metal, alkaline earth metal or ammonium cation,
a unit —$N(Z_2Z_3)$ in which $Z_2$ and $Z_3$, independently of one another, represent a hydrogen atom, a $C_1$–$C_{12}$ alkyl, a $C_3$–$C_7$ cycloalkyl, a $C_1$–$C_{12}$ alkyl substituted by an —N(RaRb) group in which Ra and Rb are as defined above or a $C_1$–$C_{12}$ alkyl substituted by one or a number of optionally esterified alcohol functional groups or alternatively $Z_2$ and $Z_3$, together with the nitrogen atom to which they are bonded, form a 5- to 7-membered heterocycle optionally containing a second heteroatom,
the said unit Q being defined according to the nature of the $R^3$ to $R^8$ substituents which it carries, namely
$Q^1$ for saturated rings, that is to say when $R^7$ and $R^8$ are hydrogen atoms,

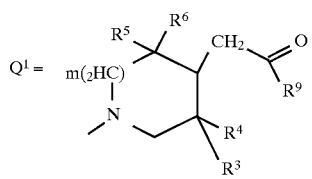

in which:
$R^3$, $R^4$, $R^5$ and $R^6$ represent a hydrogen atom or a $C_1$–$C_8$ alkyl, preferably methyl or ethyl,
m and $R^9$ are defined as above, $Q^2$ for unsaturated heterocyclic units in which the double bond is extracyclic (that is to say, when $R^7$ and $R^8$ form a double bond)

$$Q^2 = \underset{\underset{N}{|}}{m(_2HC)} \overset{R^5}{\underset{}{}}\!\!\!\!\!\!\overset{R^6}{\underset{R^4}{\underset{|}{\overset{|}{C}}}}\!\!\!\!\!\!\overset{CH_2}{\underset{R^3}{}}\!\!\!\!\!\!\overset{}{\underset{}{C}}\!\!\!\!\!\!\overset{O}{\underset{R^9}{}}$$

and, in which:
$R^3$, $R^4$, $R^5$, $R^6$, $R^9$ and m are defined as above,
$Q^3$ for unsaturated heterocyclic units in which the double bond is intracyclic (that is to say, when $R^7$ and $R^6$ form a double bond)

$$Q^3 = \underset{\underset{N}{|}}{m(_2HC)} \overset{R^5}{\underset{R^4}{\underset{|}{\overset{}{C}}}}\!\!\!\!\!\!\overset{CH_2}{\underset{R^3}{}}\!\!\!\!\!\!\overset{}{\underset{}{C}}\!\!\!\!\!\!\overset{O}{\underset{R^9}{}}$$

and, in which:
$R^3$, $R^4$, $R^5$, $R^9$ and m are defined as above,
$R^8$ represents a hydrogen atom,
and $Q^4$ for unsaturated heterocyclic units in which the intracyclic double bond is formed by $R^7$ and $R^4$, $$Q^4 = \underset{\underset{N}{|}}{m(_2HC)} \overset{R^5}{\underset{R^3}{\overset{R^6}{\overset{|}{C}}}}\!\!\!\!\!\!\overset{CH_2}{\underset{}{}}\!\!\!\!\!\!\overset{}{\underset{}{C}}\!\!\!\!\!\!\overset{O}{\underset{R^9}{}}$$

in this unit,
$R^3$, $R^5$, $R^6$, $R^9$ and m are defined as above,
$R^8$ represents a hydrogen atom.
Moreover, the pairs of radicals $R^3$–$R^4$, $R^5$–$R^6$ and $R^3$–$R^5$ can, independently of one another, also represent a 5- to 7-membered ring or heterocycle.

The compounds of the invention are either in the racemic form or in the enantiomerically pure form. Some of them also possess cis/trans-type isomerism. The present invention also relates to the pharmaceutically acceptable salts of the compounds of formula (I).

The compounds of formula (I) above are novel compounds with the exception of the compounds of formula (I) in which:
either $R^1$ and $R^2$ are hydrogen or the methyl group or $R^1$ is the methyl group or a chlorine atom and $R^2$ is hydrogen, A is the $(CH_2)_2$ group, Q is $Q^1$ or $Q^2$ in which $R^3$, $R^4$, $R^5$ and $R^6$ are each hydrogen, m is equal to 1 and $R^9$ is an ethoxy or hydroxyl group,
or $R^1$ and $R^2$ are each a fluorine atom in the 4-position, A is a $(CH_2)_2$ group, Q is $Q^1$ or $Q^2$ in which $R^3$, $R^4$, $R^5$ and $R^6$ are each hydrogen, m is equal to 1 and $R^9$ is an ethoxy group.

The compounds of formula (I) above, in which either $R^1$ and $R^2$ are hydrogen or the methyl group or $R^1$ is the methyl group and $R^2$ is hydrogen and A, Q, m and $R^9$ are as defined above, are described in Application EP-A1-259,227 as compounds having antihistaminic and antispasmodic properties. The compounds of formula (I) above in which $R^1$ and $R^2$ are each a fluorine atom in the 4-position and A, Q, m and R9 are as defined above are described in Application JP-A-2,212,472 as compounds having antihistaminic and antiallergic properties.

Another subject of the invention is therefore the above novel compounds.

In the present description, the term $C_1$–$C_6$, $C_1$–$C_4$ or $C_1$–$C_8$ alkyl denotes a saturated straight- or branched-chain aliphatic hydrocarbon residue containing 1 to 6, 1 to 4 or 1 to 8 carbon atoms respectively. The preferred alkyls for the purposes of the invention are the methyl or ethyl groups.

The $C_2$–$C_8$ alkylene or alkenylene chains are saturated or unsaturated, linear or branched aliphatic chains having 2 to 8 carbon atoms.

"Halogen" denotes one of the four halogens: F, Cl, Br and I. $R_1$ and $R_2$, when they represent a halogen, are preferably F or Cl.

The cations M are alkali metal or alkaline-earth metal cations, such as, for example, Na, K, Ca or Mg, or ammoniums, such as diethyl- or cyclohexyl-ammonium.

"5- or 7-membered heterocycle" in particular denotes the following rings: pyrrolidine, piperidine or perhydroazepine. 5- or 7-membered heterocycle containing a second heteroatom denotes in particular the morpholino, oxazolidino, piperazino, perhydrodiazepino and diazolidino groups.

"5- to 7-membered ring" in particular denotes the following cycloalkyl units: cyclopentyl, cyclohexyl, cycloheptyl.

A preferred group of the compounds of the invention is composed of the compounds of formula (I) in which
Q is $Q^1$ or $Q^2$ in which at least one of the $R^3$, $R^4$, $R^5$ and $R^6$ radicals is other than hydrogen,
m is equal to 1,
A is the $(CH_2)_2$ group.

Advantageous compounds of general formula (I) are those which correspond to the following conditions:
$R^1$ and $R^2$, which are identical or different, are hydrogen or halogen atoms, preferably fluorine,
A is a $(CH_2)_n$ alkylene chain in which n is an integer between 3 and 6,
the heterocyclic unit Q is $Q^1$ with m equal to 0 or 1 and $R^3$, $R^4$, $R^5$ and $R^6$ represent a hydrogen atom or a methyl.

Other advantageous compounds are those in which Q represents a unit $Q^1$ in which at least one of the $R^3$, $R^4$, $R^5$ and $R^6$ substituents is different from the other three, the said compounds being in the form of cis or trans isomers.

Other advantageous compounds are the compounds of the formula (I) in which:
$R^3$ and $R^2$ independently represent a hydrogen or a fluorine atom in the 2- or 4-position
A is an alkylene chain having 3 to 5 carbon atoms
m is equal to 1
Q is $Q^1$
$R^4$, $R^5$ and $R^6$ represent a hydrogen atom
$R^3$ is a hydrogen or a methyl or ethyl group
$R^9$ is an ethoxy unit or a hydroxyl.

Among these compounds, those in which $R^3$, $R^4$, $R^5$ and $R^6$ represent a hydrogen atom are preferred according to the invention.

Other advantageous compounds are compounds of formula (I) in which:
A is an alkylene chain having 3 to 6 carbon atoms
m is an integer equal to 0 or to 1
Q represents $Q^2$ as defined above in which at least one of the $R^3$, $R^4$, $R^5$ and $R^6$ substituents is different from the other three, the said derivatives being in the form of cis or trans isomers.

Particularly advantageous compounds are compounds of formula (I) in which:

$R^1$ and $R^2$ independently represent a hydrogen or a fluorine atom in the 2- or 4-position A is an alkylene chain having 3 to 5 carbon atoms m is equal to 1

Q is $Q^1$ $R^5$ and $R^6$ represent a hydrogen atom $R^3$ and $R^4$ are methyl or ethyl groups $R^9$ is an ethoxy unit or a hydroxyl.

The particularly preferred compounds of the invention are the compounds below, in the form of optically pure or racemic cis/trans isomers:

ethyl {1-[1-((4,4'-difluorodiphenyl)methoxy)-4-butyl]-3-methyl}piperidino-4-acetate ($R^1$=$R^2$=4-F; A=—$(CH_2)_4$—; $R^3$=$CH_3$, $R^9$=$OC_2H_5$)

ethyl {1-[1-((4,2'-difluorodiphenyl)methoxy)-4-butyl]-3-methyl}piperidino-4-acetate ($R^1$=4-F; $R^2$=2-F; A=—$(CH_2)_4$—; $R^3$=$CH_3$, $R^9$=$OC_2H_5$)

ethyl {1-[1-((4,4'-difluorodiphenyl)methoxy)-3-propyl]-3-methyl}piperidino-4-acetate ($R^1$=$R^2$=4-F; A=—$(CH_2)_3$—; $R^3$=$CH_3$, $R^9$=$OC_2H_5$)

ethyl {1-[1-((4,2'-difluorodiphenyl)methoxy)-3-propyl]-3-methyl}piperidino-4-acetate ($R^1$=4-F; $R^2$=2-F; A=—$(CH_2)_3$—; $R^3$=$CH_3$, $R^9$=$OC_2H_5$)

ethyl {1-[1-((4,4'-difluorodiphenyl)methoxy)-3-propyl]}piperidino-4-acetate ($R^1$=4-F; $R^2$=4-F; A=—$(CH_2)_3$—; $R^3$=H, $R^9$=$OC_2H_5$)

ethyl {1-[1-(diphenyl)methoxy)-5-pentyl]-3-methyl}-piperidino-4-acetate ($R^1$=$R^2$=H; A=—$(CH_2)_5$—; $R^3$=$CH_3$, $R^9$=$OC_2H_5$)

ethyl {1-[1-(4,4'-difluorodiphenyl)methoxy)-5-pentyl]-3-methyl}piperidino-4-acetate ($R^1$=$R^2$=4-F; A=—$(CH_2)_5$—; $R^3$=$CH_3$, $R^9$=$OC_2H_5$)

ethyl {1-[1-((4-fluorodiphenyl)methoxy)-3-propyl]-3-methyl}piperidino-4-acetate ($R^1$=4-F; $R^2$=H; A=—$(CH_2)_3$—; $R^3$=$CH_3$, $R^9$=$OC_2H_5$)

ethyl {1-[1-((4-fluorodiphenyl)methoxy)-4-butyl]-3-methyl}piperidino-4-acetate ($R^1$=4-F; $R^2$=H; A=—$(CH_2)_4$—; $R^3$=$CH_3$, $R^9$=$OC_2H_5$)

ethyl {1-[1-((4-fluorodiphenyl)methoxy)-5-pentyl]-3-methyl}piperidino-4-acetate ($R^1$=H; $R^2$=4-F; A=—$(CH_2)_5$—; $R^3$=$CH_3$, $R^9$=$OC_2H_5$)

ethyl {1-[1-((4,4'-difluorodiphenyl)methoxy)-4-butyl]-3,3-dimethyl}piperidino-4-acetate ($R^1$=$R^2$=4-F; A=—$(CH_2)_4$—; $R^3$=$CH_3$, $R^4$=$CH_3$, $R^9$=$OC_2H_5$)

{1-[1-((4,4'-difluorodiphenyl)methoxy)-4-butyl]-3-methyl}piperidino-4-acetic acid ($R^1$=$R^2$=4-F; A=—$(CH_2)_4$—; $R^3$=$CH_3$, $R^9$=OH)

{1-[1-((4,4'-difluorodiphenyl)methoxy)-4-butyl]-3,3-dimethyl}piperidino-4-acetic acid ($R^1$=$R^2$=4-F; A=—$(CH_2)_4$—; $R^4$=$CH_3$, $R^3$=$CH_3$, $R^9$=OH)

The derivatives of formula (I) in which:

$R^9$ is a unit —OZ, in which $Z_1$ is as defined above with the exception of hydrogen A, m, $R^1$, $R^2$ and $R^3$ are as defined above, Q is, without distinction, $Q^1$, $Q^2$, $Q^3$ or $Q^4$ can be prepared according to Process A by condensation of the nitrogenous heterocycles II in which m, $R^4$, $R^5$, $R^3$, $R^6$ and $R^9$ are defined above with the chlorinated intermediates (III) for which A, $R^1$ and $R^2$ correspond to the preceding definition, in the presence of potassium or sodium carbonate and of a catalytic amount of potassium or sodium iodide in an aromatic solvent, such as benzene or toluene, in dimethylformamide, in acetonitrile or in 2-butanone.

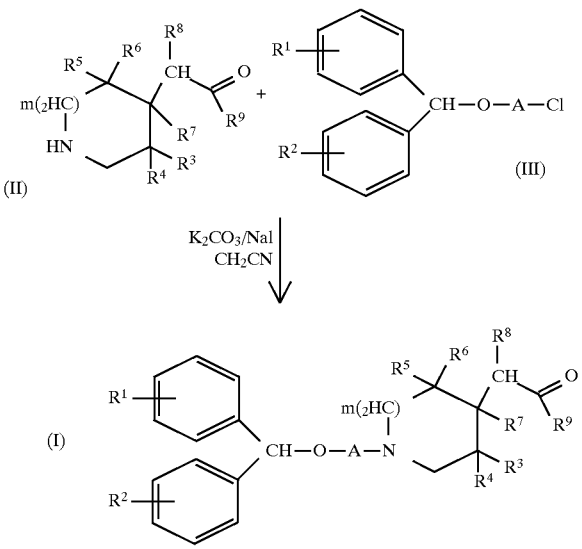

Process A

The derivatives of formula (I) in which:

$R^9$ represents a unit —$OZ_1$ with $Z_1$=H

A, m, $R^1$, $R^2$, $R^3$, $R^4$, $R^5$, $R^6$, $R^7$ and $R^8$ correspond to the general definition, are prepared according to Process B by hydrolysis of the corresponding esters in which $R^9$ is a $C_1$–$C_8$ alkoxy with 10% strength potassium hydroxide in an aqueous/alcoholic medium at room temperature or at 40° C.

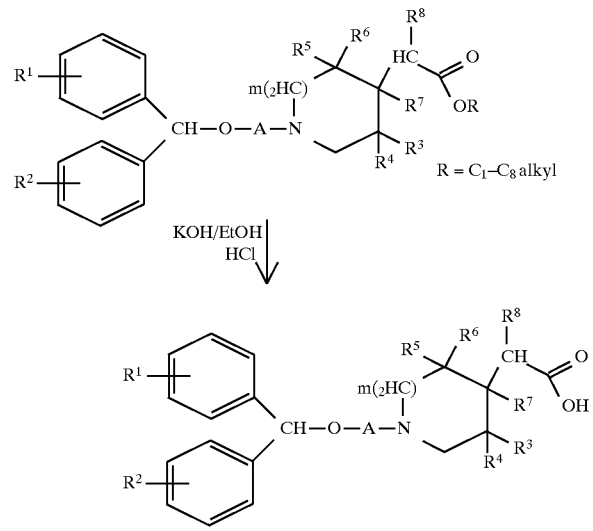

Process B

The compounds obtained can be isolated in the acid form or in the form of alkaline-earth metal salts or salts of linear or cyclic, primary, secondary or tertiary amines.

The derivatives of formula (I) in which:

$R^9$ represents a unit —$N(Z_2Z_3)$

A, m, $R^1$, $R^2$, $R^3$, $R^4$, $R^5$, $R^6$, $R^7$, $R^8$, $Z_2$ and $Z_3$ are as defined above, are synthesized conventionally by amidation of the corresponding acids I described above with linear or cyclic, mono- or disubstituted amines of general formula (IV)

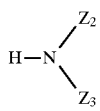
IV in which $Z_2$ and $Z_3$ are as defined above, in the presence of dicyclohexylcarbodiimide (DCC) and 1-hydroxybenzotriazole in solvents such as tetrahydrofuran or acetonitrile or in chlorinated solvents, such as methylene chloride or chloroform, according to Process C:

Process C

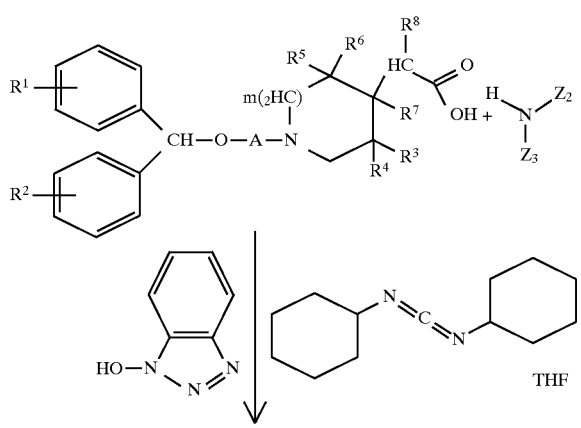

-continued
Process C

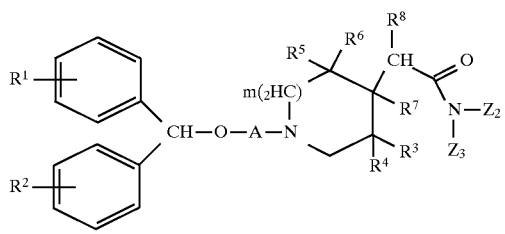

The derivatives of general formula (Ia) in which:

$R^9$ represents a unit —$OZ_1$ or —OM with $Z_1$ and M defined as above,

Q represents $Q^1$,

A is a $(CH_2)_n$ alkylene chain, n, m, $R^1$, $R^2$, $R^3$, $R^4$, $R^5$, $R^6$, $R^7$ and $R^8$ are defined as above, are obtained according to Process D by hydrogenation of the ethylenic compounds Ib, Ic and Id in the presence of a catalyst, such as Raney nickel or platinum, in a lower alcohol, such as methanol, ethanol or isopropanol. There action is carried out at 50° C. approximately and under 60 to 100 bar of pressure.

Process D

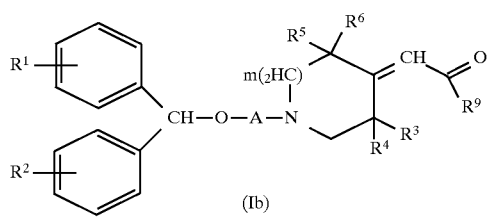
(Ib)

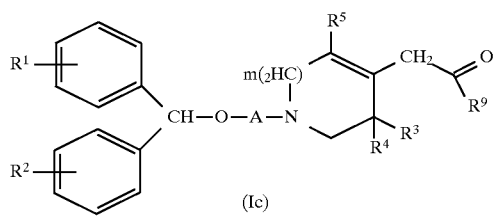
(Ic)

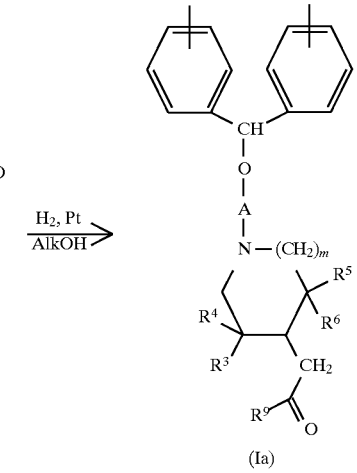
(Ia)

-continued

Process D

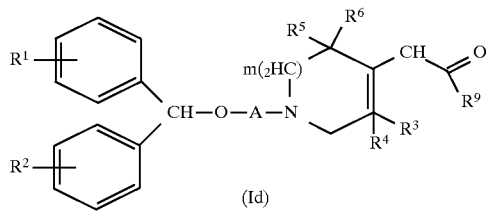

(Id)

The derivatives of formula (I) of the invention in which:
$R^9$ is a unit $-OZ_1$, $Z_1$ is a $C_1-C_{12}$ alkyl group or a $C_3-C_7$ cycloalkyl group
Q represents $Q^2$,
A, m, $R^1$, $R^2$, $R^4$, $R^5$ and $R^6$ correspond to the general definition,
$R^3$ is a hydrogen atom or a $C_1-C_6$ alkyl group, preferably methyl or ethyl, can easily be obtained by Proces E which comprises the Wittig-Horner reaction between the alkyl phosphonoacetates V and the ketone derivatives VI in which
A, m, $R^1$, $R^2$, $R^4$, $R^5$ and $R^6$ are as defined above, in a solvent such as tetrahydrofuran (THF) or dimethoxyethane (DME) or in an aromatic solvent, preferably toluene, at room temperature and in the presence of two equivalents of sodium hydride as basic agent.

Process E is summarized in the following way:

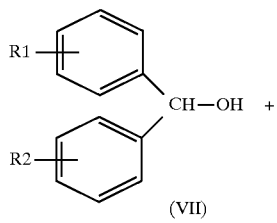

(VII)

$$HO-A-X \xrightarrow{APTS, Ar-H}$$

(VIII)

Process E

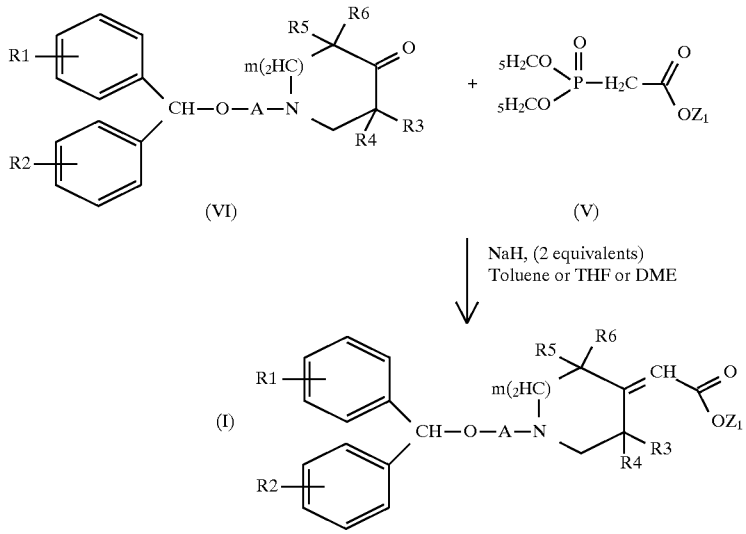

The halogenated derivatives (III) are conventionally prepared by condensation of the corresponding benzhydrols (VII) with ω-haloalcohols (VIII) in an aromatic solvent (ArH), such as benzene or toluene, in the presence of a catalytic amount of p-toluenesulfonic acid (PTSA) and by distilling off the water as it is formed.

-continued

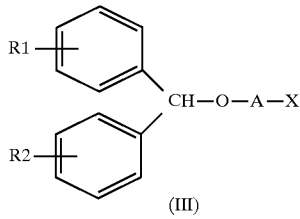

(III)

The benzhydrols (VII) used are either commercially available or obtained by methods described in the literature, namely by,

- reduction of the corresponding benzophenones (IX) by sodium borohydride in ethanol or methanol, or
- Grignard reaction between the substituted enzaldehydes (X) and the phenylmagnesium derivatives XI) in any crousethyl ether.

The compounds of formula XII in which Q is $Q^1$, $Q^2$, $Q^3$ or $Q^4$ in which at least one of the $R^3$, $R^4$, $R^5$ and $R^6$ substituents, if it exists, is other than hydrogen, in the racemic or optically pure form and/or in the form of cis/trans isomers, are novel compounds and represent a further aspect of the invention.

Among these compounds, the compounds of formula XII in which:

m is equal to 1,

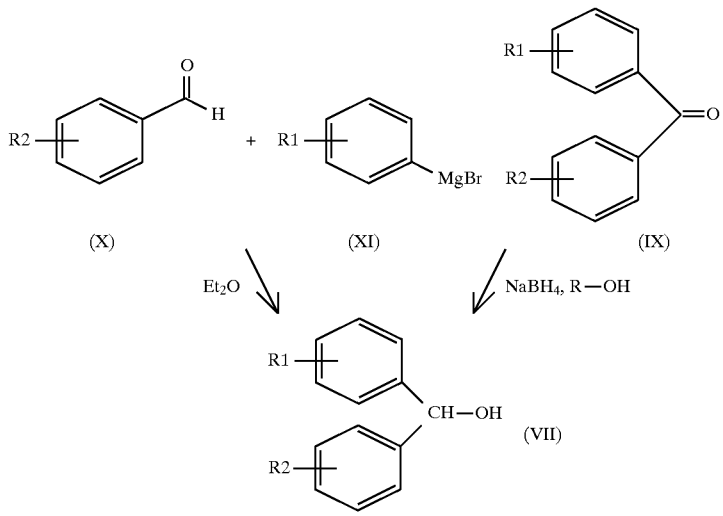

The heterocycles of general formula (II), corresponding to the units Q–H

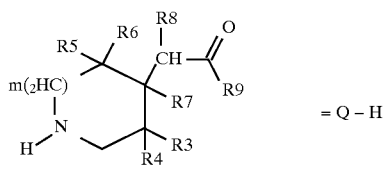

Q being, without distinction, $Q^1$, $Q^2$, $Q^3$ or $Q^4$, can be obtained by hydrogenolysis of the corresponding benzyl compounds (XII) in the presence of palladium in ethanol, at ambient temperature and ambient pressure.

Q is $Q^1$ with $R^3$ is a methyl group, $R^4$ is a methyl group or a hydrogen atom and $R^5$ and $R^6$ each represent a hydrogen atom, $R^9$ is an ethoxy group, are preferred compounds according to the invention.

The saturated compounds (II) for which:

Q is the radical $Q^1$, m, $R^3$, $R^4$, $R^5$, $R^6$ and $R^9$ correspond to the general definition, can be prepared by catalytic debenzylation and hydrogenation of the ethylenic heterocycles (XIIa), (XIIb) and (XIIc),

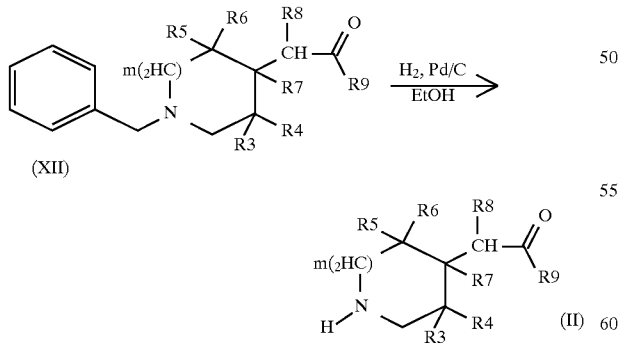

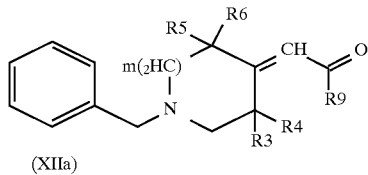

(XIIa)

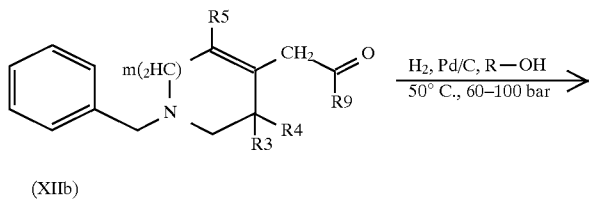

(XIIb) (II)

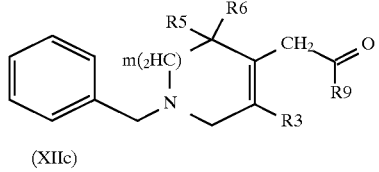

(XIIc)

under 60 to 100 bar of pressure at 50° C., in the presence of palladium/C, in an alcohol such as methanol or ethanol.

The compounds of formula (II) in which:

Q is $Q^1$,
m is equal to 1,
$R^3$ is a methyl group,
$R^4$ is hydrogen or a methyl group,
$R^5$ and $R^6$ are hydrogen,
$R^9$ is an ethoxy group, in the racemic or optically pure form and/or in the form of cis/trans isomers, are novel compounds which represent another aspect of the invention.

Among these compounds, ethyl 3,3-dimethylpiperidine-4-acetate of formula (II) in which Q is $Q^1$,
m is equal to 1,
$R^5$ and $R^6$ are hydrogen,
$R^3$ and $R^4$ are methyl groups,
$R^9$ is an ethoxy group, is a preferred compound.

The piperidine (II) for which:

Q is the radical $Q^1$,
m is equal to 1,
$R^3$ is a methyl group,
$R^4$, $R^5$ and $R^6$ represent a hydrogen atom,
$R^9$ is an ethoxy, can easily be obtained by catalytic hydrogenation of the hydrochloride of the substituted pyridine XX. In the case where the alkyl group is methyl, when the catalyst used is platinum oxide, the reduction results in a piperidine containing less than 10% of trans isomer. When the catalyst is Palladium/C, the percentage of trans isomer is approximately 20%.

Ethyl 3-methylpyridine-4-acetate XX is prepared by ethoxycarbonylation of the carbanion of lutidine generated by lithium diisopropylamide (LDA) in tetrahydrofuran, according to the following reaction sequence:

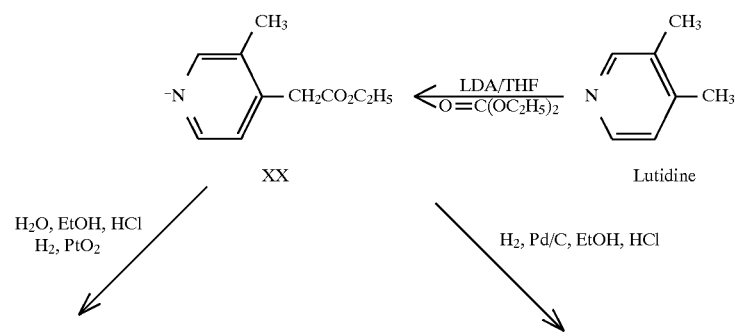

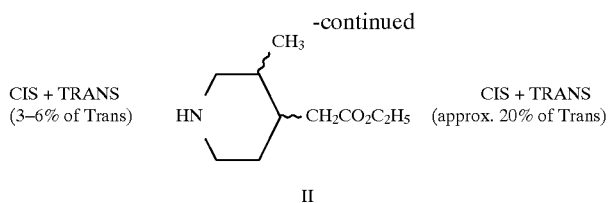

The benzyl derivatives (XIIa), (XIIb) and (XIIc) for which:

$R^9$ is a unit —$OZ_1$ in which $Z_1$ is a $C_1$–$C_{12}$ alkyl or a $C_3$–$C_7$ cycloalkyl, m, $R^3$, $R^4$, $R^5$ and $R^6$ correspond to the general definition, can be obtained, as a mixture or pure, by a Wittig-Horner reaction between the alkyl phosphonoacetates (V) described above and the ketones (XIII).

$R^4$, $R^5$, and $R^6$ are hydrogen atoms, $Z_1$ is defined as above, the reaction, carried out in the presence of 2 equivalents of sodium hydride, in an aromatic solvent, for example toluene, at room temperature, results in a mixture of the three ethylenic compounds (XIIa, b, c) which are separated by chromatography on silica gel.

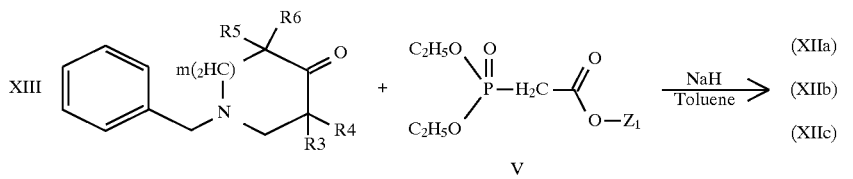

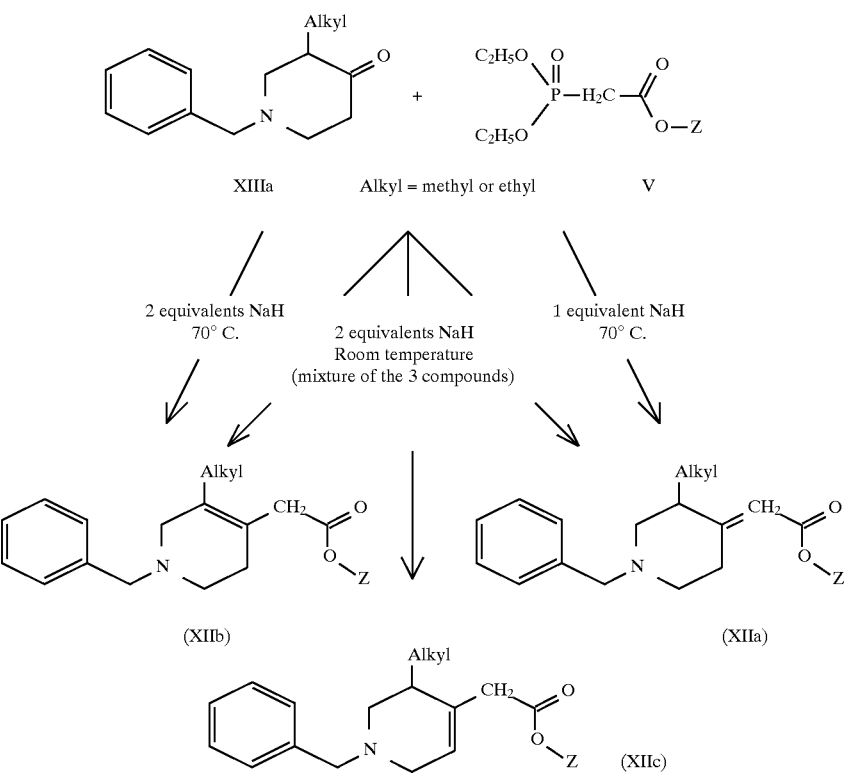

In the case where:

m is equal to 1, $R^3$ represents a methyl or ethyl radical,

The use of a single equivalent of sodium hydride in toluene at 70° C. results in the single ethylenic compound (XIIa).

When the reaction is carried out at 70° C. with 2 equivalents of NaH, the pure ethylenic compound (XIIb) is obtained.

The intermediates (XIIIa) defined in the preceding paragraph are prepared by the method described in J. Org. Chem. 57, 10, 1992, by alkylation with alkyl iodide in dimethoxyethane of the benzyl-piperidones of formula (XIV) in which R represents the ethyl or methyl group, followed by decarboxylation in hydrochloric acid medium.

The benzylpiperidone XIIIc is a novel compound which forms part of the invention. It can also be obtained from 1-benzyl-3-ethoxycarbonyl-3-methyl-4-piperidone XIX, according to the reaction sequence adapted from the procedure described in J. Org. Chem., 57, 2794–2803, 1992 and specified below:

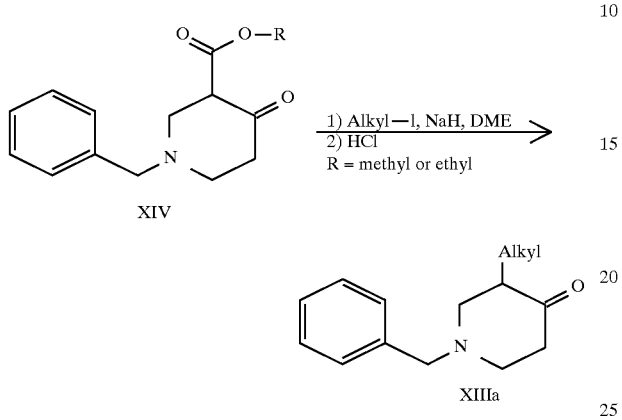

The benzylpiperidone of general formula XIII in which:
m is equal to 1
$R^3$ and $R^4$ represent a methyl radical,
$R^5$ and $R^6$ are hydrogen atoms,
can be prepared by methylation with methyl iodide of the carbanion of commercial benzyl-4-piperidone XIIIb or of the piperidone XIIIa in which the alkyl radical is the methyl group.

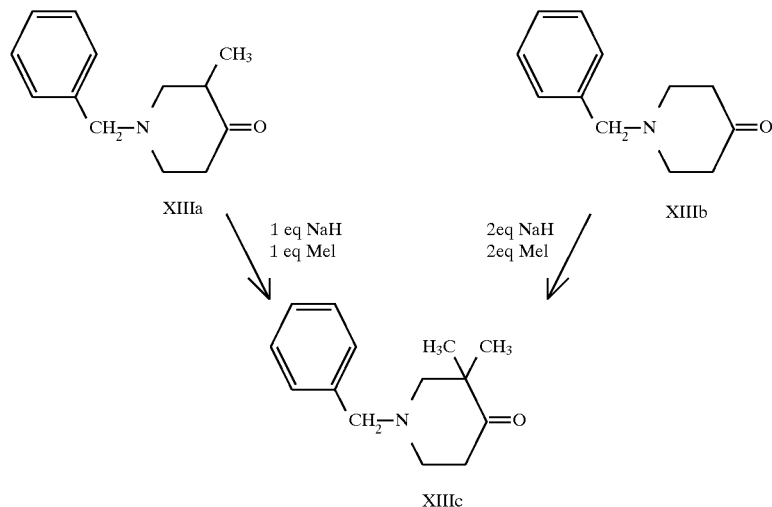

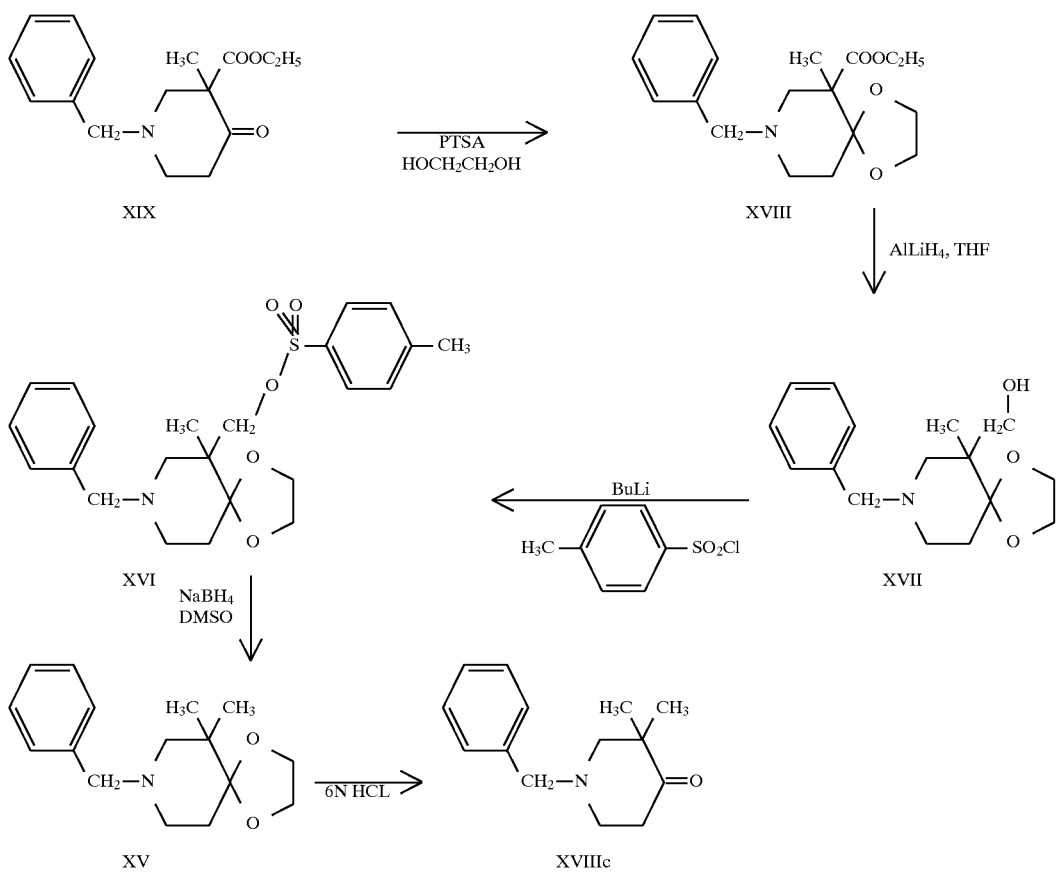

The compounds of the invention of general formula (I) and the synthetic intermediates in which the heterocyclic unit Q is $Q^1$ or $Q^2$ in which at least one of the $R^3$, $R^4$, $R^5$ and $R^6$ substituents is different from the others possess cis/trans-type isomerism. The cis derivatives and the trans derivatives were isolated by chromatography on silica gel and characterized by their nuclear magnetic resonance spectra.

In addition to this isomerism, these same compounds have at least two asymmetric carbons. The enantiomers are isolated by fractional crystallization of their optically active salts.

The acid addition salts of the derivatives of formula I according to the invention can be obtained by conventional processes with acids commonly used to obtain pharmaceutically acceptable salts, such as hydrochloric, hydrobromic, oxalic, maleic, fumaric, succinic and methanesulfonic acids.

The preferred salts, for the purposes of the invention, are the hydrochlorides, the oxalates or the maleates.

The pharmacological study of the substituted nitrogenous heterocycle derivatives of the invention has revealed a significant psychotropic activity. This activity has been displayed in particular in the following pharmacological and biochemical tests: study of the spontaneous motility, of the rectal temperature, of the antagonism of the sleep induced by barbital, of the potentiation of the toxicity of yohimbine, of the antagonism of the hypothermia and of the palpebral ptosis induced by reserpine, of the antagonism of the hypothermia induced by apomorphine administered at a high dose, of the potentiation of the effects of L-Dopa, of the caudal suspension test, of the swimming test and of the inhibition of the re-uptake of dopamine, of noradrenaline and of serotonin.

The compounds of the invention are active with respect to these tests or some of these tests at low doses after intraperitoneal administration and after oral administration.

In addition, the advantageous properties of the compounds of the invention are not accompanied, to any significant degree, by harmful side effects. In fact, the search for the approximate lethal dose 50, carried out according to the Lorke method, shows that the products of the invention do not result in death after oral administration at doses greater than 500 mg.Kg$^{-1}$.

These products are therefore particularly appropriate for the development of pharmaceutical compositions.

The pharmaceutical compositions of the invention contain an effective amount of at least one substituted nitrogenous heterocycle derivative as defined above, in combination with an inert pharmaceutical vehicle.

Advantageous pharmaceutical compositions contain these derivatives alone or in combination with antidepressant, anxiolytic or neuroleptic psychotropic medicaments or L-Dopa.

On account of their antidepressant activity, these pharmaceutical compositions can be used in the following therapeutic indications: depressive states, compulsive obsessional disorders, panic attack, memory disorders, schizophrenia, Parkinson's disease, state of dependence and obesity.

The pharmaceutical compositions of the invention can be administered in different forms, namely by the injectable, nasal, transdermal, rectal or oral route.

For oral administration, recourse is had in particular to tablets, pills, lozenges, hard gelatin capsules, soft capsules, drops or alternatively to liposomes. These compositions advantageously contain from 1 to 100 mg per unit taken.

Other administration forms comprise solutions which are injectable intravenously, subcutaneously or intramuscularly, in sterile or sterilizable solutions. These solutions contain 1 to 50 mg per unit taken. By way of indication, the posology which can be used in man corresponds to the following doses: thus, for example, 5 to 500 mg/day are administered to the patient in one or a number of intakes.

The invention is also targeted at the biological reagents, the active principles of which are composed of the substituted nitrogenous heterocycle derivatives defined above.

These reagents can be used as reference or standards in studies of possible psychotropic activities.

Finally, the invention is targeted at the potential metabolytes of the compounds of the invention resulting from animal or human metabolism.

Other characteristics and advantages of the invention will become apparent in the following examples relating to the preparation of substituted nitrogenous heterocycle derivatives and to the study of their psychotropic activity.

In the illustrative examples 1 to 72, the derivatives prepared were identified and characterized from studying their nuclear magnetic resonance and mass spectra and from their elemental analysis. The structures of these compounds according to the invention are shown in Tables 1 and 2.

TABLE 1

Derivative of general formula I (Q = Q1)

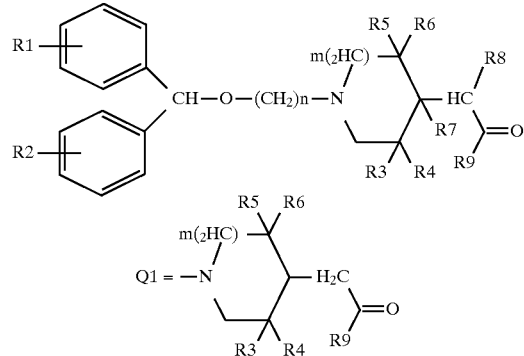

| Example | Cis/Trans | m | n | $R^1$ | $R^2$ | $R^3$ | $R^4$ | $R^5$ | $R^6$ | $R^9$ |
|---|---|---|---|---|---|---|---|---|---|---|
| 1 | Cis | 1 | 2 | H | H | $CH_3$ | H | H | H | $OC_2H_5$ |
| 2 | Cis | 1 | 2 | 4-F | 4-F | $CH_3$ | H | H | H | $OC_2H_5$ |
| 3 | Cis | 1 | 2 | 4-$CH_3$ | H | $CH_3$ | H | H | H | $OC_2H_5$ |
| 4 | Trans | 1 | 2 | 4-$CH_3$ | H | $CH_3$ | H | H | H | $OC_2H_5$ |
| 5 | Cis | 1 | 2 | 4-Cl | 4-Cl | $CH_3$ | H | H | H | $OC_2H_5$ |
| 6 | Trans | 1 | 2 | 4-Cl | 4-Cl | $CH_3$ | H | H | H | $OC_2H_5$ |
| 7 | Cis | 1 | 2 | 4-F | 2-F | $CH_3$ | H | H | H | $OC_2H_5$ |
| 8 | Cis | 1 | 2 | 4-Cl | H | $CH_3$ | H | H | H | $OC_2H_5$ |
| 9 | Trans | 1 | 2 | 4-Cl | H | $CH_3$ | H | H | H | $OC_2H_5$ |
| 10 | Cis | 1 | 2 | H | H | $C_2H_5$ | H | H | H | $OC_2H_5$ |
| 11 | Trans | 1 | 2 | H | H | $C_2H_5$ | H | H | H | $OC_2H_5$ |
| 12 | Cis | 1 | 2 | 4-F | 4-F | $C_2H_5$ | H | H | H | $OC_2H_5$ |
| 13 | Trans | 1 | 2 | 4-F | 4-F | $C_2H_5$ | H | H | H | $OC_2H_5$ |
| 14 | | 1 | 3 | H | H | H | H | H | H | $OC_2H_5$ |
| 15 | Cis | 1 | 3 | H | H | $CH_3$ | H | H | H | $OC_2H_5$ |
| 16 | Cis | 1 | 3 | 4-Cl | H | $CH_3$ | H | H | H | $OC_2H_5$ |
| 17 | Cis | 1 | 3 | 4-F | 4-F | $CH_3$ | H | H | H | $OC_2H_5$ |
| 18 | Cis | 1 | 3 | 4-Cl | 4-Cl | $CH_3$ | H | H | H | $OC_2H_5$ |
| 19 | Trans | 1 | 3 | H | H | $CH_3$ | H | H | H | $OC_2H_5$ |
| 20 | Trans | 1 | 3 | 4-F | 4-F | $CH_3$ | H | H | H | $OC_2H_5$ |
| 21 | Trans | 1 | 3 | 4-Cl | H | $CH_3$ | H | H | H | $OC_2H_5$ |
| 22 | Trans | 1 | 3 | 4-Cl | 4-Cl | $CH_3$ | H | H | H | $OC_2H_5$ |
| 23 | Cis | 1 | 3 | 4-F | 2-F | $CH_3$ | H | H | H | $OC_2H_5$ |
| 24 | Trans | 1 | 3 | 4-F | 2-F | $CH_3$ | H | H | H | $OC_2H_5$ |
| 25 | Trans | 1 | 3 | 4-$CH_3$ | H | $CH_3$ | H | H | H | $OC_2H_5$ |
| 26 | Cis | 1 | 3 | 4-$CH_3$ | H | $CH_3$ | H | H | H | $OC_2H_5$ |
| 27 | Cis | 1 | 3 | H | H | $C_2H_5$ | H | H | H | $OC_2H_5$ |
| 28 | Trans | 1 | 3 | H | H | $C_2H_5$ | H | H | H | $OC_2H_5$ |
| 29 | Cis | 1 | 3 | 4-Cl | 3-Cl | $C_2H_5$ | H | H | H | $OC_2H_5$ |
| 30 | Trans | 1 | 3 | 4-Cl | 3-Cl | $C_2H_5$ | H | H | H | $OC_2H_5$ |
| 31 | Cis | 1 | 3 | 4-F | 4-F | $C_2H_5$ | H | H | H | $OC_2H_5$ |
| 32 | trans | 1 | 3 | 4-F | 4-F | $C_2H_5$ | H | H | H | $OC_2H_5$ |
| 33 | Cis | 1 | 4 | 4-F | 4-F | $CH_3$ | H | H | H | $OC_2H_5$ |

TABLE 1-continued

Derivative of general formula I (Q = Q1)

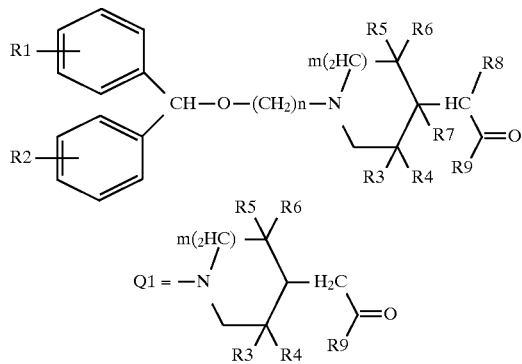

| Example | Cis/Trans | m | n | R¹ | R² | R³ | R⁴ | R⁵ | R⁶ | R⁹ |
|---|---|---|---|---|---|---|---|---|---|---|
| 34 | Trans | 1 | 4 | 4-F | 4-F | $CH_3$ | H | H | H | $OC_2H_5$ |
| 35 | Trans | 1 | 4 | 4-F | 2-F | $CH_3$ | H | H | H | $OC_2H_5$ |
| 36 | Cis | 1 | 4 | 4-F | 2-F | $CH_3$ | H | H | H | $OC_2H_5$ |
| 37 | Cis | 1 | 4 | 4-F | 4-F | $CH_3$ | H | H | H | OH |
| 38 | Trans | 1 | 4 | 4-F | 4-F | $C_2H_5$ | H | H | H | $OC_2H_5$ |
| 39 | Cis | 1 | 4 | 4-F | 4-F | $C_2H_5$ | H | H | H | $OC_2H_5$ |
| 40 | Cis | 1 | 4 | 4-F | 2-F | $C_2H_5$ | H | H | H | $OC_2H_5$ |
| 41 | Trans | 1 | 4 | 4-F | 2-F | $C_2H_5$ | H | H | H | $OC_2H_5$ |
| 42 | Cis | 1 | 3 | 4-F | 4-$CF_3$ | $CH_3$ | H | H | H | $OC_2H_5$ |
| 43 | Trans | 1 | 3 | 4-F | 4-$CF_3$ | $CH_3$ | H | H | H | $OC_2H_5$ |
| 44 | Cis | 1 | 3 | 4-F | 3-$CF_3$ | $CH_3$ | H | H | H | $OC_2H_5$ |
| 45 | Trans | 1 | 3 | 4-F | 3-$CF_3$ | $CH_3$ | H | H | H | $OC_2H_5$ |
| 46 | Cis | 1 | 3 | 4-F | 3-F | $CH_3$ | H | H | H | $OC_2H_5$ |
| 47 | Trans | 1 | 3 | 4-F | 3-F | $CH_3$ | H | H | H | $OC_2H_5$ |
| 48 | Cis | 1 | 3 | 4-F | H | $CH_3$ | H | H | H | $OC_2H_5$ |
| 49 | Trans | 1 | 3 | 4-F | H | $CH_3$ | H | H | H | $OC_2H_5$ |
| 50 | Trans | 1 | 3 | 4-$CF_3$ | H | $CH_3$ | H | H | H | $OC_2H_5$ |
| 51 | Cis | 1 | 3 | 4-$CF_3$ | H | $CH_3$ | H | H | H | $OC_2H_5$ |
| 52 | Cis | 1 | 3 | 4-F | 2-F | $CH_3$ | H | H | H | $OC_2H_5$ |
| 53 | Trans | 1 | 3 | 4-F | 4-F | $CH_3$ | H | H | H | OH |
| 54 | | 1 | 4 | 4-F | 4-F | H | H | H | H | $OC_2H_5$ |
| 55 | | 1 | 3 | 4-F | 4-F | H | H | H | H | $OC_2H_5$ |
| 56 | Cis | 1 | 4 | 4-F | H | $CH_3$ | H | H | H | $OC_2H_5$ |
| 57 | Trans | 1 | 4 | 4-F | H | $CH_3$ | H | H | H | $OC_2H_5$ |
| 58 | | 1 | 2 | H | H | H | H | H | H | $NH(CH_2)_2N(Et)_2$ |
| 59 | Cis | 1 | 5 | 4-F | 4-F | $CH_3$ | H | H | H | $OC_2H_5$ |
| 60 | Trans | 1 | 5 | 4-F | 4-F | $CH_3$ | H | H | H | $OC_2H_5$ |
| 61 | Cis | 1 | 4 | H | H | $CH_3$ | H | H | H | $OC_2H_5$ |
| 62 | Trans | 1 | 4 | H | H | $CH_3$ | H | H | H | $OC_2H_5$ |
| 63 | Cis | 1 | 4 | 4-F | 4-F | $CH_3$ | H | H | H | $N(Et)_2$ |
| 64 | Cis + Trans | 0 | 4 | 4-F | 4-F | $CH_3$ | H | H | H | $OC_2H_5$ |
| 65 | — | 0 | 4 | 4-F | 4-F | H | H | H | H | $OC_2H_5$ |
| 66 | — | 1 | 4 | 4-F | 4-F | $CH_3$ | $CH_3$ | H | H | $OC_2H_5$ |
| 67 | — | 1 | 3 | 4-F | 4-F | $CH_3$ | $CH_3$ | H | H | $OC_2H_5$ |
| 68 | — | 1 | 4 | 4-F | 4-F | $CH_3$ | $CH_3$ | H | H | OH |

TABLE 2

Derivatives of general formula (Q = Q2)

[Chemical structure diagrams]

| Example | Cis/trans | m | n | R¹ | R² | R³ | R⁴ | R⁵ | R⁶ | R⁹ |
|---------|-----------|---|---|-----|-----|-----|----|----|----|------|
| 69 | Cis | 1 | 3 | 4-F | 4-F | CH₃ | H | H | H | OC₂H₅ |
| 70 | Trans | 1 | 3 | 4-F | 4-F | CH₃ | H | H | H | OC₂H₅ |
| 71 | Cis | 1 | 2 | H | H | CH₃ | H | H | H | OC₂H₅ |
| 72 | Trans | 1 | 2 | H | H | CH₃ | H | H | H | OC₂H₅ |

Process A to D for the synthesis of the derivatives of formula I, as well as the access routes to the synthetic intermediates, are illustrated below for a few compounds.

PROCESS A

Examples 33 and 34

Preparation of the cis and trans derivatives of ethyl 1-[1-(4, 4'-difluorodiphenyl-methoxy)]butyl]-3-methylpiperidino-4-acetate
{$R^1$ and $R^2$=4-F, m=1, A=(CH$_2$)n, n=4, Q=Q$^1$, $R^4$, $R^5$ and $R^6$=H, $R^3$=CH$_3$, $R^9$=O—C$_2$H$_5$}.

The mixture of 1-[1-(4,4'-difluorodiphenyl)methoxy]-4-chlorobutane (9.16 g, 0.029M), ethyl 3-methyl-piperidin-4-acetate [sic] (5.42 g, 0.029M), K$_2$CO$_3$ (8.8 g, 0.064M), NaI (1 g, 0.006M) and acetonitrile (150 ml) is brought to reflux for 24 hours. After cooling and filtering, the solvent is evaporated and the residue is taken up in water and CH$_2$Cl$_2$.

The organic phase is dried, concentrated and chromatographed on Silica (eluent: AcOEt/cyclohexane: 20/80). Two products are obtained:

Cis(6.2 g, Yd.=46%) and Trans (3 g, Yd.=22%).
Oxalate

The base is dissolved in ethyl alcohol or isopropanol. One equivalent of oxalic acid, dissolved in the alcohol, is added and the salt crystallizes.

Cis M.p.=132° C.
Trans M.p.=127° C.

PROCESS B

Example 37

Preparation of cis-1-[1-(4,4'-difluorodi-phenylmethoxy) butyl]-3-methylpiperidine-4-acetic acid
{$R^1$ and $R^2$=4-F, m=1, A=(CH$_2$)n, n=4, Q=Q$^1$, $R^4$, $R^5$ and $R^6$=H, $R^3$=CH$_3$, $R^9$=OH}

The ester (1.30 g, 0.003M), in 30 ml of 10% alcoholic potassium hydroxide, is left under magnetic stirring at room temperature. The reaction is monitored by TLC. The alcohol is evaporated, 30 ml of water are added and acidification is carried out to pH=5.4. The product is extracted with CH$_2$Cl$_2$. 1.1 g of product is obtained (Yd.=90%).

$^1$H NMR: 0.95 (d,3H); 1.5–3 (m,16H); 3.41 (t,2H); 5.27 (s,1H); 6.8–7.5 (m,8H); 11.2 (s,1H).
Oxalate:

1.1 g of the above product is dissolved in 2-butanone (10 ml), 0.23 g of oxalic acid in 2-butanone is added and the crystallized salt is filtered off and dried in an oven under vacuum. M.p.=98° C.

PROCESS C

Example 58

Preparation of [1-(diphenylmethoxy-2-ethyl)piperidino]-4-(1,1-diethylamino-2-ethyl)acetamide
{$R^1$ and $R^2$=H, m=1, A=(CH$_2$)n [sic], n=2, Q=Q$^1$, $R^3$, $R^4$, $R^5$ and $R^6$=H, $R^9$=NH—(CH$_2$)$_2$—N(C$_2$H$_5$)$_2$}

[1-(1,1-Diphenylmethoxy)ethyl)piperidine-4-acetic acid ($R^1$ and $R^2$=H, m=1, A=(CH$_2$)n, n=2, Q=Q$^1$, $R^3$, $R^4$, $R^5$ and $R^6$=H, $R^9$=OH) (3.53 g, 0.01M), diethylaminoethylamine (1.16 g, 0.01M) and 1-hydroxy-benzotriazole (1.35 g, 0.01M), in solution of 5 ml of anhydrous tetrahydrofuran, are placed in a reactor. The mixture is cooled to 0° C. with an ice bath and dicyclohexylcarbodiimide (DCC) (2.17 g, 0.0105M) is added slowly, with stirring. At the end of the addition, the reaction mixture is stirred for 24 hours at room temperature.

After filtering, the solution is washed with water and the expected product is extracted with methylene chloride. 2.9 g of crude oil are obtained, which oil is isolated in the hydrochloride form. After releasing with sodium carbonate, in the presence of benzene, the product is chromatographed on neutral alumina (methylene chloride).

After purification, 1.3 g (Yield=35%) of pure compound are isolated, which compound is identified by NMR.

The hydrochloride is prepared by addition of 0.29 ml of a 10N solution of hydrochloric acid in ethanol.

PROCESS D

Examples 15 and 19

Preparation of the cis and trans isomers of ethyl [1-(3-(diphenylmethoxy)propyl)-3-methyllpiperidine-4-acetate
{$R^1$ and $R^2$=H, m=1, A=(CH$_2$)n, n=3, Q=Q$^1$, $R^4$, $R^5$ and $R^6$=H, $R^3$=CH$_3$, $R^9$=O—C$_2$H$_5$}

3.52g of Raney nickel, in suspension in 80 ml of absolute ethanol, and 7.9 g of ethyl [1-(3-(diphenyl-methoxy)propyl) -3-methyl]piperid-4-ylideneacetate are placed in an autoclave.

The ethylenic compound is hydrogenated under 100 bar of pressure at room temperature for 24 hours. After filtering off the catalyst, the solvent is evaporated. 9.3 g of a mixture of cis and trans compounds are obtained.

The pure cis and trans isomers are isolated by chromatography on Silica under the conditions described in Process A.

PROCESS E

Examples 69 and 70

Preparation of the cis and trans isomers of ethyl 1-[1-(4,4'-(difluoro-diphenylmethoxy)propyl]-3-methyl]piperid-4-ylideneacetate
{$R^1$ and $R^2$=4-F, m=1, A=(CH$_2$)n, n=3, Q=Q$^2$, $R^4$, $R^5$ and $R^6$=H, $R^3$=CH$_3$, $R^3$=O—C$_2$H$_5$}

Triethyl phosphonoacetate (3.6 g, 0.016M) is added dropwise to a suspension of sodium hydride (0.67 g, 0.028M) in 10 ml of toluene, cooled to 16° C., in a 100 ml three-necked flask. Throughout the addition, the temperature is maintained at a temperature of between 16° and 20° C.

The reaction mixture is left at room temperature for one hour and then 1-[1-(4,4'-difluorodiphenylmethoxy)-propyl]-3-methylpiperidine-4-one (5 g, 0.013M), in 10 ml of toluene, is added dropwise while maintaining the temperature at between 16° and 20° C. After the end of the addition, the reaction mixture is left stirring at room temperature. The reaction is monitored by TLC, water is added and extraction is carried out with toluene. The organic phase is dried, concentrated and chromatographed on Silica (eluent: AcOEt/Cyclohexane: 20/80).

Two products are obtained: Cis (1.1 g, Yd.=18%) and Trans (3 g, Yd.=51%).

$^1$H NMR: Cis (Compound 69): 1,2 (d,3H); 1.25 (t,3H); 1.6–3.1 (m,11H); 3.5 (t,2H); 4.15 (q,2H); 5.3 (s,1H); 5.55 (s,1H); 6.80–7.50 (m,8H); Trans (Compound 70): 1,05 (d,3H); 1.27 (t,3H); 1.60–3 (m,11H); 3.48 (t,2H); 4.15 (q,2H); 5.3 (s,1H); 5.61 (s,1H); 6.80–7.50 (m,8H).

Preparation of the synthesis intermediates
Preparation of 1-[1-(4,4'-difluorodiphenylmethoxy)-propyl]-3-methylpiperidine-4-one
Compound VI: {$R^1$ and $R^2$=4-F, m=1, A=$(CH_2)_n$, n=3, $R^4$, $R^5$ and $R^6$=H, $R^3$=$CH_3$}

The mixture of 1-[4,4'-difluorodiphenylmethoxy]-3-chloropropane (12 g, 0.04M), 3-methylpiperidine-4-one hydrochloride (6.05 g, 0.04M), potassium carbonate (14 g, 0.10M), sodium iodide (1 g, 0.006M) and acetonitrile (200 ml) is brought to reflux for 24 hours.

After cooling and filtering, the solvent is evaporated and the residue is taken up in water and $CH_2Cl_2$; the organic phase is dried, concentrated and chromatographed on Silica (eluent: AcOEt/Cyclohexane: 30/70). 10 g of oil are obtained.
Yd.=66%.

$^1$H NMR: 1,1 (d,2H); 1.6–3.2 (m,11H); 3.50 (t,2H); 5.3 (s,1H); 6.80–7.45 (m,8H)

Preparation of 1-benzyl-3,3-dimethyl-4-piperidone
Compound XIIIc): {m=1, $R^5$ and $R^6$=H, $R^3$ and $R^4$=$CH_3$}
From 1-benzyl-4-piperidone XIIIb or 1-benzyl-3-methyl-4-piperidone XIIIa 1. From 1-benzyl-4-piperidone (XIIIb)

Sodium hydride (21.5 g, 0.89M), in suspension in 500 ml of tetrahydrofuran, is placed in a three-necked flask under a nitrogen atmosphere. After cooling to 0° C. using an ice bath, a solution of 1-benzyl-4-piperidone (85 g, 0.45M) in 200 ml of THF and iodomethane (191.25 g, 1.35M), dissolved in 200 ml of THF, are successively added dropwise. The temperature is maintained at 0° C. throughout the addition.

After the end of the addition, the reaction mixture is kept stirring at this temperature for 3 H and then 24 H at room temperature.

20 ml of a saturated sodium sulfate solution and 500 ml of toluene are added.

Drying is carried out over magnesium sulfate and the solution is concentrated under reduced vacuum.

The residue is taken up in ethyl ether and, after filtering and concentrating, the residual oil is chromatographed on silica (eluent: methylene chloride/cyclohexane 10/90). 55 g of pure product are obtained (Yield=56%).

$^1$H NMR: 1.1(s,6H); 2.35(s,2H); 2.45–2.7(m,4H); 3.5(s, 2H); 7.28(m,5H).

2. From 1-benzyl-3-methyl-4-piperidone (XIIIb)
Procedure. The procedure is identical to that described above. (Yield=54%).
From 1-benzyl-3-methyl-3-etoxycarbonyl-4-piperidone (XIX)

a. 1-benzyl-3-methyl-3-ethoxycarbonylpiperidino-4-dioxolane (XVIII)

The hydrochloride of 1-benzyl-3-methyl-3-ethoxycarbonyl-4-piperidone (XIX) (34.5 g, 0.11M), ethylene glycol (21 g, 0.34M), para-toluenesulfonic acid (1 g, 0.005M) and toluene (400 ml) are heated at reflux, in a round-bottomed flask surmounted by a Dean and Stark apparatus, until the volume of water produced by the reaction has settled out (2 ml).

After cooling, cold water is added and neutralization is carried out with sodium carbonate. The organic phase is dried over sodium sulfate and then concentrated under vacuum. 29 g of product are obtained, which product is used as is.
(Crude yield=82%).

$^1$H NMR: 1.12(t, 3H); 1.2(s, 3H); 1.6–2.9(m, 6H); 3.4(s, 2H); 3.9(s, 4H); 4.10 (q, 2H); 7.2(m, 5H).

b. 1-benzyl-3-methyl-3-hydroxymethylpiperidino-4-dioxolane (XVII)

1-Benzyl-3-methyl-3-etoxycarbonylpiperidino-4-dioxolane [sic] (XVIII) (4.8 g, 0.015M), in 30 ml of anhydrous THF, is added dropwise onto lithium aluminum hydride (2.55 g, 0.067M), in 40 ml of anhydrous THF, in a three-necked flask, under a nitrogen atmosphere; the temperature is maintained at 20° C. throughout the addition. After the end of the addition, the reaction mixture is heated at reflux for 3 hours. After cooling, cold water (5 ml) and then 15% NaOH (3 ml) are added, the solid is filtered off and washed with ether, the solution is dried over sodium sulfate and concentrated under vacuum and an oily product (3 g, 0.011M) is obtained.
(Yield=72%).

$^1$H NMR: 0.8(s, 3H); 1.6–2.7(m, 6H); 3.45(s, 2H); 3.7(s, 2H); 3.95(m, 5H); 7,28 (m, 5H)

c. 1-benzyl-3-methyl-3-(p-toluensulfonyl)methyl-piperidino-4-dioxolane (XVI)

The solution of 1-benzyl-3-methyl-3-hydroxymethyl-piperidino-4-dioxolane (XVII) (0.011M) in ether (50 ml) is cooled to 0° C. in a three-necked flask.

2.5M Butyllithium in hexane (5 ml, 0.013M) is added dropwise at this temperature and the reaction mixture is stirred for 10 minutes. The chloride of paratoluenesulfonic acid (2.8 g, 0.0154M) in 20 ml of ether is added dropwise while maintaining the temperature at 0° C. The reaction mixture is stirred at this temperature for 5 hours, is diluted with 15% NaOH and extracted with ether. The extract is dried and concentrated under vacuum and 4.31 g of crude product are obtained.
(Yield=92%).

$^1$H NMR: 0.98(s, 3H) 1.65(t, 2H); 2.1–2.7(m, 7H); 3.50(s, 2H); 3.87(s, 4H); 4.1(s, 2H); 7.3(m, 7H); 7.75(d, 2H).

d. 1-benzyl-3,3-dimethylpiperidin-4-dioxolane (XV)
1 - E e n z y l - 3 - m e t h y l - 3 - p a r a -toluensulfonylmethylpiperidino-4-dioxolane (XVI) (70 g, 0.162M) is dissolved in 800 ml of DMSO in a round-bottomed flask and sodium borohydride (19 g, 0.486M) is added portionwise. After the end of the addition, the reaction mixture is heated at 85° C. and the reaction is monitored by TLC. After cooling, 15% sodium hydroxide is added and extraction is carried out. The solvent is concentrated under vacuum and 39 g of crude product are obtained.
(Crude yield=92%).

$^1$H NMR: 0.98(s, 6H); 1.8(t, 2H); 2.22(s, 2H); 2.5(t, 2H); 3.47(s, 2H); 3.93(s, 4H); 7.31(m, 5H).

e. 1-benzyl-3,3-dimethyl-4-piperidone (XIIIc) 1-Benzyl-3,3-dimethylpiperidino-4-dioxolane XV) (43 g, 0.165M) in hydrochloric acid (6N) (500 ml) and acetone (500 ml) in a round-bottomed flask is brought to reflux for 12 hours. The reaction mixture is concentrated under vacuum, neutralized with sodium carbonate and extracted with ether.

The organic phase is dried over sodium sulfate and then concentrated under vacuum. The product is chromatographed on a silica column (eluent: cyclohexane/ethyl acetate 97.5/2.5). 23 g of oily product are obtained (Yield= 64%).

$^1$H NMR: 1.1(s, 6H); 2.35(s, 2H); 2.45–2.7(m, 4H); 3.5(s, 2H); 7.28(m, 5H)

Preparation of ethyl 3-methylpiperidine-4-acetate
Compound II: {m=1, Q=Q$^1$, R$^4$, R$^5$ and R$^6$=H, R$^3$=CH$_3$, R$^9$=OC$_2$H$_5$}
A—Via ethylenic benzyl derivatives XIIa (Q=Q$^2$), XIIb (Q=Q$^3$) and/or XIIc (Q=Q$^3$)

The hydrochlorides of XIIa (Q=Q$^2$), XIIb (Q=Q$^3$) and/or XIIc (Q=Q$^3$); (m=1, R$^4$, R$^5$ and R$^6$=H, R$^3$=CH$_3$, R$^9$=OC$_2$H$_5$) (30.1 g, 0.1M), 2 g of 10% Pd/C and 150 ml of absolute ethanol are subjected, in an autoclave, to a hydrogen pressure of 70 bar and heated at 60° C. The reaction is monitored by TLC and GC-MS. The catalyst is filtered off, the solvent is evaporated, the solid obtained is neutralized with Na$_2$CO$_3$ and the product is extracted with CH$_2$Cl$_2$ and then distilled.
B.p. 9 mmHg=112°–114° C.

$^1$H NMR: 0.9(d,3H); 1.15 (t,3H); 1.56- (s,NH); 1.3–3.2 (m, 9H); 4.15 (q,2H).
B—Via lutidine
1. Preparation of ethyl 3-methyl-4-pyridineacetate. (XX)

931 ml of butyllithium (1.6M) in solution in hexane are charged into a reactor under a nitrogen atmosphere. The solution is cooled to −60° C. (acetone/solid carbon dioxide).

229 ml of diisopropylamine are slowly added at −60° C. with stirring and the reaction mixture is left for 30 minutes at this temperature.

80 g of 3,4-lutidine, dissolved beforehand in 1000 ml of anhydrous tetrahydrofuran, are then added while maintaining the temperature at −60° C. (±2° C.). At the end of the addition, the reaction mixture is stirred for 30 minutes at this temperature and then 219 ml of diethyl carbonate, in solution in 1000 ml of anhydrous tetrahydrofuran, are subsequently added while stirring well. At the end of the addition, the reaction mixture is left stirring for 30 minutes at −60° C. and the temperature is allowed to rise for 2 hours with stirring.

1500 ml of toluene and 150 ml of a saturated sodium sulfate solution are added to the reaction mixture. Stirring is carried out until most of the precipitate has dissolved. Drying is carried out over MgSO$_4$, filtering is carried out and the filtrate is evaporated to dryness. The residue is taken up in 500 ml of ether and extracted with a normal hydrochloric acid solution. The aqueous phase is washed 3 times with 300 ml of ether and then neutralized with an aqueous ammonia solution in the presence of 500 ml of dichloromethane. The aqueous phase is again extracted twice with 300 ml of dichloromethane. The extracts are combined, dried over MgSO$_4$ and then filtered. After evaporating the solvent, the compound is distilled under 2.5 mmHg. 112 g of crude product are obtained, which product is distilled under reduced vacuum (B.p. 2.5 mmHg=104°–106° C.) (Yield: 83.7%)

1H NMR : 1,25(t, 3H); 2,3(s, 3H); 3.6(s, 2H); 4.2(q, 9H); 7.15(d, 1H); 8.4(m, 2H)

2. Reduction of ethyl 3-methyl-4-pyridineacetate (XX)

The hydrochloride of ethyl 3-methyl-4-pyridineacetate (XX) (50 g, 0.23 mol), 75 ml of water, 75 ml of ethanol, 0.75 ml of concentrated (37%) hydrochloric acid and the catalyst are subjected, in an autoclave, to a hydrogen pressure of the order of 70 bar at room temperature. The reaction is monitored by TLC.

With PtO$_2$ as catalyst, the reaction takes place in 12 hours; in contrast, with Pd/C (10%), it requires 48 hours. The catalyst is filtered off and the solvent is evaporated. The solid obtained is taken up in 150 ml of water. The aqueous phase is neutralized with a saturated NaOH solution and the product is extracted with 300 ml of ether. The extraction with ether is repeated twice (2×150 ml) after having saturated the aqueous phase with NaCl. The extracts are combined, dried over MgSO$_4$, filtered and concentrated to dryness. The residual oil is distilled under reduced vacuum [sic] (B.p. 9 mm Hg=112°–114° C.).

| Catalyst used | Time | Relative % of cis derivative | Relative % of trans derivative | Overall yield (cis + trans) |
|---|---|---|---|---|
| PtO$_2$ | 12 h | 96% | 4% | 84% |
| Pd/C (10%) | 48 h | 82% | 18% | 81% |

Wittig-Horner reaction between 1-benzyl-3-methyl-4-piperidone and triethyl phosphonoacetate:
Preparation of the ethylenic compounds XIIa. XIIb and XIIc a) 2 equivalents of NaH at room temperature Triethyl phosphonoacetate (7.95 g, 0.035M) is added dropwise to a suspension of sodium hydride (1.47 g, 0.60M) in 20 ml of toluene, cooled to 16° C., in a 100 ml three-necked flask. The temperature is maintained below 20° C. throughout the addition. The reaction mixture is left at room temperature for one hour; 1-benzyl-3-methylpiperidone (6 g, 0.029M) in 20 ml of toluene is then added dropwise while maintaining the temperature at below 20° C. After the end of the addition, the reaction mixture is left stirring at room temperature.

The reaction is monitored by TLC until the starting material has disappeared. The reaction mixture is cooled and neutralized with ice. The organic phase is dried over magnesium sulfate and concentrated under vacuum. The oil obtained is chromatographed on Silica (eluent: AcOEt/Cyclohexane/Et$_3$N:5/95/0.2).

b) 2 equivalents of NaH at 70° C.

The preparation is carried out in the same way as in a) but, after the end of the addition of 1-benzyl-3-methyl-4-piperidone, the reaction mixture is heated at 70° C.

c) 1 equivalent of NaH at 70° C.

The preparation is carried out in the same way as in b).

| Conditions | Product | Yield |
|---|---|---|
| a | XIIa + XIIb + XIIc | 75% |
| b | XIIb | 65% |
| c | XIIa | 70% |

$^1$H NMR: XIIa cis: 1.12 (d,3H); 1.16 (t,3H); 1.5–3.2 (m,7H); 3.45 (s,2H); 4.10 (q,2H); 5.57 (s,1H); 7.30 (m,5H). XIIa trans: 1.05 (d,3H); 1.25 (t,3H); 1.8–2.85 (m,7H); 3.48 (s,2H); 4.10 (q,2H); 5.61 (s,1H); 7.30 (m,5H). XIIb: 1,23 (t,3H); 1.61 (s,3H); 2.2 (m,CH$_2$); 2.51 (m,2H); 2.88 (s,CH$_2$); 3.02 (s,CH$_2$CO); 3.56 (s,CH$_2$Ar); 4.10 (q,2H); 7.30 (m,5H). XIIc: 1(d,3H); 1,23(t,3H); 2.1–2.7 (m,3H); 3 (m,4H); 3.55 (s,2H); 4.12 (q,2H); 5.51 (t,1H); 7.30 (m,5H).

Preparation of 3-trifluoromethyl-4-fluoro-diphenylmethanol

Compound VII: $\{R^1=4\text{-F}, R^2=3\text{-CF}_3\}$.

Magnesium (3.2 g, 0.133M) is covered with anhydrous ether, a few drops of 3-trifluoromethylbromobenzene are added and the reaction is initiated with an iodine crystal, the solution of fluorobenzaldehyde (30 g, 0.133M) in 60 ml of ether is then added dropwise and the temperature rises until the ether refluxes. After the end of the addition, the reaction mixture is left for 3 hours at reflux.

The reaction mixture is cooled, neutralized with dilute hydrochloric acid and extracted with ether. 24.25 g of crude oil are obtained, which oil will be used as is. (Yield=99%).

$^1$H NMR: 2.57 (s, OH); 5.80 (s,1H); 6.85–7.75 (m, 8H).

Preparation of 1-[4,4'-difluorodiphenylmethoxy]-4-chlorobutane

Compound II: $\{R^1=R^2=4\text{-F}, A=(CH_2)n, n=4\}$ The mixture of 4,4'-difluorodiphenylmethanol (22 g, 0.1M), chlorobutanol (11.9 g, 0.11M), PTSA (1 g) and 150 ml of benzene is brought to reflux in a round-bottomed flask surmounted by a Dean and Stark apparatus. Once the volume of water (1.8 ml) has been isolated, the reaction mixture is cooled, water is added and extraction is carried out. 30 g of oil are obtained.
(Yield=96%)

$^1$H NMR: 1.70–1.95 (m,4H); 3.30–3.60 (m,4H); 5.28 (s, 1H); 6.80–7.40 (m, 8H)

The access routes, the nature of the salts and the melting points of the compounds 1 to 72 prepared according to the invention are summarized in Table 3.

TABLE 3

Physicochemical characteristics and preparation methods

| Example | Process | Salt | Empirical Formula | M.p. °C. |
|---|---|---|---|---|
| 1 | A,D | Oxalate | $C_{25}H_{33}NO_3.C_2H_2O_4$ | 149° C. |
| 2 | A,D | Oxalate | $C_{25}H_{31}F_2NO_3.C_2H_2O_4$ | 152° C. |
| 3 | A,D | Oxalate | $C_{26}H_{35}NO_3.C_2H_2O_4$ | 105° C. |
| 4 | A,D | Base | $C_{26}H_{35}NO_3$ | Oil |
| 5 | A,D | Oxalate | $C_{25}H_{31}Cl_2NO_3.C_2H_2O_4$ | 137° C. |
| 6 | A,D | Base | $C_{25}H_{31}Cl_2NO_3$ | Oil |
| 7 | A,D | Oxalate | $C_{25}H_{31}F_2NO_3.C_2H_2O_4$ | 152° C. |
| 8 | A,D | Oxalate | $C_{25}H_{32}ClNO_3.C_2H_2O_4$ | 122° C. |
| 9 | A,D | Base | $C_{25}H_{32}ClNO_3$ | Oil |
| 10 | A,D | Oxalate | $C_{26}H_{35}NO_3.C_2H_2O_4$ | 146° C. |
| 11 | A,D | Oxalate | $C_{26}H_{35}NO_3.C_2H_2O_4$ | 121.1° C. |
| 12 | A,D | Oxalate | $C_{26}H_{33}F_2NO_3.C_2H_2O_4$ | 144° C. |
| 13 | A,D | Oxalate | $C_{26}H_{33}F_2NO_3.C_2H_2O_4$ | 120° C. |
| 14 | A,D | Methane Sulfonate | $C_{25}H_{33}NO_3.CH_4O_3S$ | 80° C. (paste) |
| 15 | A,D | Oxalate | $C_{26}H_{35}NO_3.C_2H_2O_4$ | 158° C. |
| 16 | A,D | Oxalate | $C_{26}H_{34}ClNO_3.C_2H_2O_4$ | 145° C. |
| 17 | A,D | Oxalate | $C_{26}H_{33}F_2NO_3.C_2H_2O_4$ | 152° C. |
| 18 | A,D | Oxalate | $C_{26}H_{33}Cl_2NO_3.C_2H_2O_4$ | 142° C. |
| 19 | A,D | Oxalate | $C_{26}H_{35}NO_3.C_2H_2O_4$ | 166° C. |
| 20 | A,D | Oxalate | $C_{26}H_{33}F_2NO_3.C_2H_2O_4$ | 153° C. |
| 21 | A,D | Oxalate | $C_{26}H_{34}ClNO_3.C_2H_2O_4$ | 147° C. |
| 22 | A,D | Oxalate | $C_{26}H_{33}Cl_2NO_3.C_2H_2O_4$ | 161° C. |
| 23 | A,D | Oxalate | $C_{26}H_{33}F_2NO_3.C_2H_2O_4$ | 168° C. |
| 24 | A,D | Oxalate | $C_{26}H_{33}F_2NO_3.C_2H_2O_4$ | 169° C. |
| 25 | A,D | Oxalate | $C_{27}H_{37}NO_3.C_2H_2O_4$ | 140° C. |
| 26 | A,D | Oxalate | $C_{27}H_{37}NO_3.C_2H_2O_4$ | 132° C. |
| 27 | A,D | Oxalate | $C_{27}H_{37}NO_3.C_2H_2O_4$ | 146° C. |
| 28 | A,D | Oxalate | $C_{27}H_{37}NO_3.C_2H_2O_4$ | 101.1° C. |
| 29 | A,D | Oxalate | $C_{27}H_{35}Cl_2NO_3.C_2H_2O_4$ | 148° C. |
| 30 | A,D | Oxalate | $C_{27}H_{35}Cl_2NO_3.C_2H_2O_4$ | 127° C. |
| 31 | A,D | Oxalate | $C_{27}H_{35}F_2NO_3.C_2H_2O_4$ | 162° C. |
| 32 | A,D | Oxalate | $C_{27}H_{35}F_2NO_3.C_2H_2O_4$ | 144° C. |
| 33 | A,D | Oxalate | $C_{27}H_{35}F_2NO_3.C_2H_2O_4$ | 132° C. |
| 34 | A,D | Oxalate | $C_{27}H_{35}F_2NO_3.C_2H_2O_4$ | 127° C. |
| 35 | A,D | Oxalate | $C_{27}H_{35}F_2NO_3.C_2H_2O_4$ | 122° C. |
| 36 | A,D | Oxalate | $C_{27}H_{35}F_2NO_3.C_2H_2O_4$ | 109° C. |
| 37 | B | Oxalate | $C_{25}H_{31}F_2NO_3.C_2H_2O_4$ | 98° C. |
| 38 | A,D | Oxalate | $C_{28}H_{37}F_2NO_3.C_2H_2O_4$ | 133° C. |
| 39 | A,D | Oxalate | $C_{28}H_{37}F_2NO_3.C_2H_2O_4$ | 146.6° C. |
| 40 | A,D | Oxalate | $C_{28}H_{37}F_2NO_3.C_2H_2O_4$ | 125–6° C. |
| 41 | A,D | Oxalate | $C_{28}H_{37}F_2NO_3.C_2H_2O_4$ | 126.8° C. |
| 42 | A,D | Oxalate | $C_{27}H_{33}F_4NO_3.C_2H_2O_4$ | 141° C. |
| 43 | A,D | Oxalate | $C_{27}H_{33}F_4NO_3.C_2H_2O_4$ | 122° C. |
| 44 | A,D | Oxalate | $C_{27}H_{33}F_4NO_3.C_2H_2O_4$ | 165–166° C. |
| 45 | A,D | Oxalate | $C_{27}H_{33}F_4NO_3.C_2H_2O_4$ | 157–158° C. |
| 46 | A,D | Oxalate | $C_{26}H_{33}F_2NO_3.C_2H_2O_4$ | 154–6° C. |
| 47 | A,D | Oxalate | $C_{26}H_{33}F_2NO_3.C_2H_2O_4$ | 149.1° C. |
| 48 | A,D | Oxalate | $C_{26}H_{34}FNO_3.C_2H_2O_4$ | 130° C. |
| 49 | A,D | Oxalate | $C_{26}H_{34}FNO_3.C_2H_2O_4$ | 150.2° C. |
| 50 | A,D | Oxalate | $C_{27}H_{34}F_3NO_3.C_2H_2O_4$ | 120° C. |
| 51 | A,D | Oxalate | $C_{27}H_{34}F_3NO_3.C_2H_2O_4$ | 122° C. |
| 52 | B | Oxalate | $C_{24}H_{29}F_2NO_3.C_2H_2O_4$ | 168° C. |
| 53 | B | Oxalate | $C_{24}H_{29}F_2NO_3.C_2H_2O_4$ | 158° C. |
| 54 | A,D | Oxalate | $C_{26}H_{33}F_2NO_3.C_2H_2O_4$ | 143–4° C. |
| 55 | A,D | Oxalate | $C_{25}H_{31}F_2NO_3.C_2H_2O_4$ | 163–4° C. |
| 56 | A,D | Oxalate | $C_{27}H_{36}FNO_3.C_2H_2O_4$ | 107° C. |
| 57 | A,D | Oxalate | $C_{27}H_{36}FNO_3.C_2H_2O_4$ | 104° C. |
| 58 | C | Hydrochloride | $C_{28}H_{41}F_2NO_3.HCl$ | Oil |
| 59 | A,D | Oxalate | $C_{28}H_{37}F_2NO_3.C_2H_2O_4$ | 101.3° C. |
| 60 | A,D | Oxalate | $C_{28}H_{37}F_2NO_3.C_2H_2O_4$ | 93.8° C. |
| 61 | A,D | Oxalate | $C_{27}H_{37}NO_3.C_2H_2O_4$ | 104° C. |
| 62 | A,D | Oxalate | $C_{27}H_{37}NO_3.C_2H_2O_4$ | 99.5° C. |
| 63 | A,C | Oxalate | $C_{29}H_{40}F_2N_2O_3.C_2H_2O_4$ | 137° C. |
| 64 | A | Fumarate | $C_{26}H_{33}F_2NO_3.C_2H_4O_4$ | 92° C. |
| 65 | A | Oxalate | $C_{25}H_{31}F_2NO_3.C_2H_2O_4$ | 94.6° C. |
| 66 | A | Oxalate | $C_{28}H_{37}F_2NO_3.C_2H_2O_4$ | 120.3° C. |
| 67 | A | Oxalate | $C_{27}H_{35}F_2NO_3.C_2H_2O_4$ | 140° C. |
| 68 | B | Oxalate | $C_{26}H_{33}F_2NO_3.C_2H_2O_4$ | 73–78° C. |
| 69 | A,E | Oxalate | $C_{26}H_{31}F_2NO_3.C_2H_2O_4$ | 174° C. |
| 70 | A,E | Oxalate | $C_{26}H_{31}F_2NO_3.C_2H_2O_4$ | 195° C. |
| 71 | A,E | Oxalate | $C_{25}H_{31}NO_3.C_2H_2O_4$ | 159° C. |
| 72 | A,E | Oxalate | $C_{25}H_{31}NO_3.C_2H_2O_4$ | 164° C. |

The structures of Examples 1 to 72 according to the invention (see Table 4) and of the synthetic itermediates were confirmed from studying their NMR spectra using a Hitachi 1500 FT Fourrier transform spectrometer. The chemical shifts are measured in ppm.

TABLE 4

$^1$H NMR Spectra

| Example | (Shifts ppm, CDCl$_3$, TMS ref) |
|---|---|
| 1 | 0.95(d, 3H); 1.25(t, 3H); 1.4–2.8(m, 12H); 3.6(t, 2H); 4.15(q, 2H); 5.4(s, 1H); 7.3(m, 10H) |
| 2 | 0.95(d, 3H); 1.25(t, 3H); 1.4–2.8(m, 12H); 3.15(t, 2H); 4.15(q, 2H); 5.38(s, 1H); 6.85–7.5(m, 8H) |
| 3 | 0.95(d, 3H); 1.25(t, 3H); 1.4–2.8(m, 15H); 3.55(t, 2H); 4.15(q, 2H); 5.15(s, 1H); 7.1–7.35(m, 9H) |
| 4 | 0.85(d, 3H); 1.25(t, 3H); 1.4–3(m, 15H); 3.58(t, 2H); 4.15(q, 2H); 5.33(s, 1H); 7.1–7.35(m, 9H) |
| 5 | 0.95(d, 3H); 1.25(t, 3H); 1.4–2.8(m, 12H); 3.55(t, 2H); 4.15(q, 2H); 5.33(s, 1H); 7.27(m, 8H) |
| 6 | 0.88(d, 3H); 1.25(t, 3H); 1.4–3.1(m, 12H); 3.56(t, 2H); 4.13(q, 2H); 5.3(s, 1H); 7.27(m, 8H) |
| 7 | 0.95(d, 3H); 1.25(t, 3H); 1.4–2.8(m, 12H); 3.57(t, 2H); 4.15(q, 2H); 5.72(s, 1H); 6.8–7.6(m, 8H) |
| 8 | 0.95(d, 3H); 1.25(t, 3H); 1.4–2.8(m, 12H); 3.55(t, 2H); 4.15(q, 2H); 5.36(s, 1H); 7.28(m, 9H) |
| 9 | 0.87(d, 3H); 1.24(t, 3H); 1,4–3.1(m, 12H); 3.57(t, 2H); 4.15(q, 2H); 5.34(s, 1H); 7.28(m, 9H) |

TABLE 4-continued

¹H NMR Spectra

| Example | (Shifts ppm, CDCl₃, TMS ref) |
|---|---|
| 10 | 0.9(t, 3H); 1.23(t, 3H); 1.4–2.8(m, 14H); 3.57(t, 2H); 4.15(q, 2H); 5.37(s, 1H); 73(m, 10H) |
| 11 | 0.92(t, 3H); 1.21(t, 3H); 1.4–3.1(m, 14H); 3.6(t, 2H); 4.12(q, 2H); 5.36(s, 1H); 7.3(m, 10H) |
| 12 | 0.9(t, 3H); 1.17(t, 3H); 1.4–2.75(m, 14H); 3.55(t, 2H); 4.13(q, 2H); 5.35(s, 1H); 6.8–7.4(m, 8H) |
| 13 | 0.96(t, 3H); 1.24(t, 3H); 1.4–3.1(m, 14H); 3.62(t, 2H); 4.12(q, 2H); 5.35(s, 1H); 6.8–7.4(m, 8H) |
| 14 | 1,2(t, 3H); 1,3–3,0(m, 17H); 3,6(t, 1H); 4,1(q, 2H); 7,2(m, 10H) |
| 15 | 0.9(d, 3H); 1.24(t, 3H); 1.4–2.7(m, 14H); 3.5(t, 2H); 4.13(q, 2H); 3.33(s, 1H); 7.30(m, 10H) |
| 16 | 0.87(d, 3H); 1.24(t, 3H); 1.4–2.7(m, 14H); 3.48(t, 2H); 4.13(q, 2H); 5.29(s, 1H); 7.28(m, 9H) |
| 17 | 0.88(d, 3H); 1.24(t, 3H); 1.4–2.7(m, 14H); 3.46(t, 2H); 4.12(q, 2H); 5.27(s, 1H); 6.8–7.4(m, 8H) |
| 18 | 0.88(d, 3H); 1.25(t, 3H); 1.4–2.7(m, 14H); 3.47(t, 2H); 4.13(q, 2H); 5.27(s, 1H); 7.27(m, 8H) |
| 19 | 0.88(d, 3H); 1.23(t, 3H); 1.4–3.1(m, 14H); 3.46(t, 2H); 4.13(q, 2H); 5.28(s, 1H); 7.27(m, 9H) |
| 20 | 0.9(d, 3H); 1.25(t, 3H); 1.4–3(m, 14H); 3.46(t, 2H); 4.13(q, 2H); 5.28(s, 1H); 6.8–7.5(m, 9H) |
| 21 | 0.88(d, 3H); 1.23(t, 3H); 1.4–3(m, 14H); 3.47(t, 2H); 4.12(q, 2H); 5.28(s, 1H); 7.27(m, 9H) |
| 22 | 0.9(d, 3H); 1.24(t, 3H); 1.4–3.1(m, 14H); 3.46(t, 2H); 4.13(q, 2H); 5.26(s, 1H); 7.26(m, 8H) |
| 23 | 0.88(d, 3H); 1.22(t, 3H); 1.4–2.7(m, 14H); 3.51(t, 2H); 4.12(q, 2H); 5.66(s, 1H); 6.8–7.5(m, 8H) |
| 24 | 0.89(d, 3H); 1.24(t, 3H); 1.4–3(m, 14H); 3.5(t, 2H); 4.13(q, 2H); 5.66(s, 1H); 6.8–7.6(m, 8H) |
| 25 | 0.89(d, 3H); 1.24(t, 3H); 1.4–2.7(m, 17H); 3.48(t, 2H); 4.13(q, 2H); 5.29(s, 1H); 7.1–73(m, 9H) |
| 26 | 0.88(d, 3H); 1.24(t, 3H); 1.4–2.7(m, 17H); 3.48(t, 2H); 4.13(q, 2H); 5.29(s, 1H); 7.1–7.3(m, 9H) |
| 27 | 0.9(t, 3H); 1.23(t, 3H); 1.4–2.6(m, 16H); 3.49(t, 2H); 4.12(q, 2H); 5.32(s, 1H); 7.3(m, 10H) |
| 28 | 0.93(t, 3H); 1.23(t, 3H); 1.4–3.1(m, 16H); 3.51(t, 2H); 4.11(q, 2H); 5.33(s, 1H); 7.3(m, 10H) |
| 29 | 0.89(d, 3H); 1.24(t, 3H); 1.4–2.6(m, 16H); 3.46(t, 2H); 4.12(q, 2H); 5.25(s, 1H); 7.26(m, 8H) |
| 30 | 0.91(t, 3H); 1.25(t, 3H); 1.4–3.1(m, 16H); 3.48(t, 2H); 4.13(q, 2H); 5.27(s, 1H); 7.27(m, 8H) |
| 31 | 0.92(t, 3H); 1.24(t, 3H); 1.4–3.1(m, 16H); 3.45(t, 2H); 4.13(q, 2H); 5.29(s, 1H); 6.8–7.4(m, 8H) |
| 32 | 0.93(t, 3H); 1.24(t, 3H); 1.4–3.1(m, 16H); 3.45(t, 2H); 4.13(q, 2H); 5.29(s, 1H); 6.8–7.4(m, 8H) |
| 33 | 0.92(d, 3H); 1.25(t, 3H); 1.4–2.7(m, 16H); 3.43(t, 2H); 4.13(q, 2H); 5.28(s, 1H); 6.8–7.4(m, 8H) |
| 34 | 0.89(d, 3H); 1.25(t, 3H); 1.4–3(m, 16H); 3.43(t, 2H); 4.13(q, 2H); 5.28(s, 1H); 6.8–7.4(m, 8H) |
| 35 | 0.87(d, 3H); 1.25(t, 3H); 1.4–3(m, 16H); 3.47(t, 2H); 4.13(q, 2H); 5.66(s, 1H); 6.8–7.5(m, 8H) |
| 36 | 9.15(d, 3H); 1.24(t, 3H); 1.4–2.6(m, 16H); 3.46(t, 2H); 4.12(q, 2H); 5.65(s, 1H); 6.8–7.5(m, 8H) |
| 37 | 0.95(d, 3H); 1.5–3(m, 16H); 3.41(t, 2H); 5.27(s, 1H); 6.8–7.4(m, 8H); 11.19(s, 1H) |
| 38 | 0.94(t, 3H); 1.25(t, 3H); 1.3–3(m, 18H); 3.42(t, 2H); 4.13(q, 2H); 5.28(s, 1H); 6.8–7.4(m, 8H) |
| 39 | 0.93(t, 3H); 1.25(t, 3H); 1.3–2.6(m, 18H); 3.43(t, 2H); 4.13(q, 2H); 5.28(s, 1H); 6.8–7.4(m, 8H) |
| 40 | 0.93(t, 3H); 1.25(t, 3H); 1.3–2.6(m, 18H); 3.47(t, 2H); 4.13(q, 2H); 5.66(s, 1H); 6.8–7.5(m, 8H) |
| 41 | 0.94(t, 3H); 1.25(t, 3H); 1.3–3(m, 18H); 3.48(t, 2H); 4.13(q, 2H); 5.66(s, 1H); 6.8–7.5(m, 8H) |
| 43 | 0.9(d, 3H); 1.25(t, 3H); 1.3–3.1(m, 14H); 3.48(t, 2H); 4.13(q, 2H); 5.35(s, 1H); 6.8–7.6(m, 8H) |
| 44 | 0.87(d, 3H); 1.25(t, 3H); 1.3–2.7(m, 14H); 3.48(t, 2H); 4.13(q, 2H); 5.35(s, 1H); 6.8–7.6(m, 8H) |
| 45 | 0.84(d, 3H); 1.22(t, 3H); 1.3–3(m, 14H); 3.44(t, 2H); 4.12(q, 2H); 5.28(s, 1H); 6.8–7.6(m, 8H) |
| 46 | 0.88(d, 3H); 1.25(t, 3H); 1.3–2.7(m, 14H); 3.48(t, 2H); 4.12(q, 2H); 5.29(s, 1H); 6.8–7.4(m, 8H) |
| 47 | 0.94(d, 3H); 1.24(t, 3H); 1.3–3(m, 14H); 3.48(t, 2H); 4.13(q, 2H); 5.28(s, 1H); 6.8–7.4(m, 8H) |
| 48 | 0.88(d, 3H); 1.25(t, 3H); 1.3–2.6(m, 14H); 3.47(t, 2H); 4.12(q, 2H); 5.27(s, 1H); 6.8–7.4(m, 9H) |
| 49 | 0.88(d, 3H); 1.23(t, 3H); 1.3–3(m, 14H); 3.47(t, 2H); 4.11(q, 2H); 5.29(s, 1H); 6.8–7.4(m, 9H) |
| 50 | 0.9(d, 3H); 1.25(t, 3H); 1.3–3.1(m, 14H); 3.51(t, 2H); 4.13(q, 2H); 5.37(s, 1H); 7.2–7.6(m, 9H) |
| 51 | 0.87(d, 3H); 1.25(t, 3H); 13–2.6(m, 14H); 3.51(t, 2H); 4.13(q, 2H); 5.37(s, 1H); 7.2–7.6(m, 9H) |
| 52 | 0.98(d, 3H); 1.4–2.8(m, 14H); 3.5(t, 2H); 5.65(s, 1H); 6.9–7.5(m, 8H); 10.8(s, 1H) |
| 53 | 0.97(d, 3H); 1.4–3(m, 14H); 3.5(t, 2H); 5.27(s, 1H); 6.9–7.3(m, 8H); 9.8(s, 1H) |
| 54 | 1.24(t, 3H); 13–3(m, 17H); 3.42(t, 2H); 4.12(q, 2H); 5.27(s, 1H); 6.8–7.4(m, 8H) |
| 55 | 1.25(t, 3H); 1.3–3(m, 15H); 3.46(t, 2H); 4.13(q, 2H); 5.29(s, 1H); 6.8–7.4(m, 8H) |
| 56 | 9.2(d, 3H); 1.24(t, 3H); 1.3–2.6(m, 16H); 3.44(t, 2H); 4.13(q, 2H); 5.30(s, 1H); 6.8–7.3(m, 9H) |
| 57 | 0.89(d, 3H); 1.24(t, 3H); 1.3–3(m, 16H); 3.44(t, 2H); 4.13(q, 2H); 5.30(s, 1H); 6.8–7.4(m, 9H) |
| 58 | 1(t, 6H); 1.3–3.8(m, 19H); 3.3(q, 2H); 3.55(t, 2H); 5.35(s, 1H); 7.3(m, 10H) |
| 59 | 0,95(d, 3H); 1.25(t, 3H); 1.3–2,7(m, 18H); 3.4(t, 2H); 4.13(q, 2H); 5.3(s, 1H); 6,85–7.4(m, 8H) |
| 60 | 0,9(d, 3H); 1.25(t, 3H); 1.3–2,7(m, 18H); 3.4(t, 2H); 4.13(q, 2H); 5.3(s, 1H); 6,8–7.5(m, 8H) |
| 61 | 0,9(d, 3H); 1.25(t, 3H); 1.3–2,7(m, 16H); 3.5(t, 2H); 4.13(q, 2H); 5.3(s, 1H); 7.35(m, 10H) |
| 62 | 0,9(d, 3H); 1.25(t, 3H); 1.3–3(m, 16H); 3.5(t, 2H); 4.13(q, 2H); 5.3(s, 1H); 7.13(m, 10H) |
| 63 | 0,9–1.25(m, 11H); 1.4–2,8(m, 14H); 3.2–3.5(m, 6H); 5.3(s, 1H); 6.8–7.4(m, 8H) |
| 64 | 0,9(d, 3H); 1.27(t, 3H); 1.46–3(m, 14H); 3.3(t, 2H); 4.05(q, 2H); 5.2(s, 1H); 6.7–7.3(m, 8H) |
| 65 | 1.24(t, 3H); 1.4–3(m, 15H); 3.4(t, 2H); 4.1(q, 2H); 5.3(s, 1H); 6.8–7.4(m, 8H) |
| 66 | 0,86(s, 6H); 1.25(t, 3H); 1.4–3(m, 15H); 3.4(t, 2H); 4.1(q, 2H); 5.3(s, 1H); 6.8–7.4(m, 8H) |
| 67 | 0,83(s, 6H); 1.24(t, 3H); 1.4–3(m, 13H); 3.5(t, 2H); 4.1(q, 2H); 5.3(s, 1H); 6.8–7.4(m, 8H) |
| 68* | 0,9(s, 6H); 1,4–3,5(m, 17H); 5.48(s, 1H); 7–7, 6(m, 8H) |
| 69 | 1.2(d, 3H); 1.25(t, 3H); 1.4–3(m, 11H); 3.5(t, 2H); 4.1(q, 2H); 5.3(s, 1H); 5.6(s, 1H); 6.8–7.5(m, 8H) |
| 70 | 1.1(d, 3H); 1.3(t, 3H); 1.4–3(m, 11H); 3.5(t, 2H); 4.15(q, 2H); 5.3(s, 1H); 5.6(s, 1H); 6.8–7.5(m, 8H) |
| 71 | 1.2(d, 3H); 1.25(t, 3H); 1.4–3(m, 9H); 3.57(t, 2H); 4.15(q, 2H); 5.4(s, 1H); 5.55(s, 1H); 7.3(m, 10H) |
| 72 | 1.05(d, 3H); 1.25(t, 3H); 1.6–3(m, 9H); 3.6(t, 2H); 4.15(q, 2H); 5.37(s, 1H); 5.6(s, 1H); 7.3(m, 10H) |

*Spectrum of the oxalate

PHARMACOLOGICAL STUDIES

1) Animals used:

The animals used are mice of the NMRI strain and Wistar rats sourced from Ifa-Credo (Les Oncins France).

The housing conditions are as follows: artificial light 12/12 in a non-reversed cycle, temperature of the animal houses 22° C.±2, humidity 55±15%.

The animals receive UAR A 04C10 feed, tap water "ad libitum" and undergo a period of acclimatization of 6 days before the studies.

2) Approximate lethal dose 50 according to the Lorke method (Archives of Toxicology, 54, 275–287, 1983)

The tested product is administered to 3 groups of three mice at doses of 5, 50 and 500 mg.kg$^{-1}$ by the intraperitoneal route or by the oral route. The number of dead animals is recorded 24 hours after administration. A computerized calculation method enables 4 new doses administered to 4 groups of 1 mouse to be determined. The number of dead animals is also recorded after this last treatment and enables the approximate LD$_{50}$ to be calculated.

The substituted nitrogenous heterocycle derivatives of the invention exhibit $LD_{50}$ values from 100 to 300 mg.kg$^{-1}$ after intraperitoneal administration and $LD_{50}$ values greater than 500 mg.kg$^{-1}$ after oral administration.

3) Spontaneous motility (Arch. Int. Pharmacodyn. 158, 212–221, 1965)

The animals are placed in transparent plexiglas boxes which are introduced into the actimeter 30 minutes after treatment by the intraperitoneal route and 60 minutes after administration by the oral route. The activity of the animals is objectified by the number of passages through two light beams placed perpendicularly. These passages are recorded by counters and the number of passages is noted 30 minutes and 60 minutes after introduction of the plexiglas boxes into the actimeter. The activity of the treated animals is compared with that of a control group.

The substituted nitrogenous heterocycle derivatives of the invention have a moderate activity with respect to the spontaneous motility of the mouse. However, the products of Examples 33 to 41 significantly increase this motility from a dose of 4 mg.kg$^{-1}$ I.P. or P.O. This effect is dose-dependent.

4) Barbital sleep (J. Pharmacol. (Paris) 13, 241–252, 1982)

The animals are treated and then, depending on the route used, receive a dose of 200 mg.kg$^{-1}$ I.P. of barbital 30 or 60 minutes later, the control group receives distilled water, a reference group receives caffeine 8 mg.kg$^{-1}$ IP and another control group diazepam 1 mg.kg$^{-1}$.

The time for falling asleep and the duration of sleep of each mouse are recorded individually. The treated animals are compared with the control group.

The substituted nitrogenous heterocycle derivatives of the invention have little or no activity with respect to the sleep induced by barbital in the mouse; however, the products of Examples 33 to 41 decrease the barbital sleep from a dose of 4 mg.kg$^{-1}$ IP or PO in a dose dependent way.

5) Potentiation of the toxicity of yohimbine (Brit. J. Pharmacol. 21, 51–66, 1963)

The animals are treated with the product to be tested administered by the intraperitoneal route or by the oral route and receive a dose of yohimbin of 25 mg.kg$^{-1}$ I.P. 30 or 45 minutes later. The number of dead animals is recorded 24 h later in each treated group and compared with the mortality of a control group treated with distilled water.

The substituted nitrogenous heterocycle derivatives of the invention increase the toxicity of yohimbine from a dose of 4 mg.kg$^{-1}$ administered by the interperitoneal route or by the oral route.

6) Antagonism of the hypothermia and of the palpebral ptosis induced by reserpine (J. Pharmacol. 8, 333–350, 1977)

The animals are treated with the test products 60 minutes before administration of a dose of 2 mg.kg$^{-1}$ of reserpine. At 4, 4.5, 5, 5.5 and 6 hours after administration of the reserpine, the palpebral ptosis is graded from 0 to 4 for each eye and the rectal temperature is recorded. A control group treated with distilled water and a reference group treated with 20 mg.kg$^{-1}$ of desipramine are used in each study.

The substituted nitrogenous heterocycle derivatives of the invention decrease the hypothermia induced by reserpine from a dose of 4 mg.kg$^{-1}$ and decrease the palpebral ptosis from a dose of 8 mg.kg$^{-1}$.

7) Antagonism of the hypothermia induced by apomorphine 16 mg.kg$^{-1}$ (J. Pharmacol., 14, 93–97, 1983)

The product studied is administered by the intraperitoneal route or by the oral route 30 minutes or 60 minutes before intraperitoneal injection of a dose of 16 mg.kg$^{-1}$ of apomorphine, 20 minutes after this administration the stereotypic behaviors are graded from 0 to 3 and the righting reflexes from 0 to 1, and 10 minutes after this grading the rectal temperatures are recorded. The results of the treated groups are compared with a control group which receives distilled water. Desipramine 20 mg.kg$^{-1}$ I.P. is used as reference standard.

The substituted nitrogenous heterocycle derivatives of the invention antagonize the hypothermia induced by apomorphine from a dose of 4 mg.kg$^{-1}$ administered by the intraperitoneal route or by the oral route.

8) Potentiation of the effects of L-Dopa (N.Y. Acad. Sciences 107, 1068, 1963)

The animals are treated with the studied product administered by the oral route; 30 minutes later, they receive 150 mg.kg$^{-1}$ I.P. of L-Dopa.

30 minutes after this injection, salivation, agitation and aggressiveness are graded from 1 to 3. The results obtained with the treated animals are then compared with those observed with the control animals which have received distilled water.

The substituted nitrogenous heterocycle derivatives of the invention potentiate the effects of L-Dopa from a dose of 8 mg.kg$^{-1}$.

9) Stereotypic behaviors (J. Pharmacol., 3, 235–238, 1972)

The animals are treated by the intraperitoneal route or by the oral route and then, 30 or 60 minutes after this treatment, the stereotypic behaviors are graded from 0 to 3, every 10 minutes for 2h 30, by studying the intensity of the sniffing, chewing, licking, and the like. The results are compared with those of a control group which receives distilled water.

The substituted nitrogenous heterocycle derivatives of the invention induce stereotypic behaviors from a dose of 30 mg.kg$^{-1}$ administered by the intraperitoneal route or by the oral route.

10) Group toxicity (J. Pharmacol., 87, 214–217)

The animals are treated with the product to be tested and then placed, in groups of 10, in a small plexiglas cage. The mortality is recorded 24 hours after treatment. The substituted nitrogenous heterocycle derivatives of the invention do not cause group toxicity even when administered at a dose corresponding to $\frac{1}{3}$ of the approximate $LD_{50}$.

11) Forced swimming test (Nature 266, 730–732, 1977)

The animals are treated by the intraperitoneal route or by the oral route 30 or 60 minutes before the test. The animals are placed in a crystallizing dish filled with water and the time during which they remain immobile is clocked. The immobility time is then compared with that of the control group treated with distilled water. Imipramine 25 mg.kg$^{-1}$ I.P. is used as reference product. The potentially antidepressant products decrease the immobility time of the mice thus immersed.

The substituted nitrogenous heterocycle derivatives of the invention decrease the immobility time of the animals from a dose of 4 mg.kg$^{-1}$ administered by the intraperitoneal route or by the oral route.

12) Caudal suspension test on the mouse (Psychopharmacology, 85, 367–370, 1985)

The animals are treated with the study product by the intraperitoneal route or by the oral route 30 or 60 minutes before the test. The animals are then suspended by the tail and their immobility time is automatically recorded by a computer system. The immobility times are then compared with those of a control group treated with distilled water.

Imipramine 25 mg.kg$^{-1}$ is used as reference product. The potentially antidepressant products decrease the immobility time of the mice.

The substituted nitrogenous heterocycle derivatives of the invention decrease, in a dose-dependent way, the immobility time from a dose of 0.5 mg.kg$^{-1}$ administered by the intraperitoneal route.

13) Inhibition of dopamine re-uptake Membrane preparation 13 to 15 g of fresh pig striatum are homogenized in 200 ml of Tris 50 mM and 120 mM of NaCl at pH=7.4 buffer.

The mixture is centrifuged and the pellet is collected and frozen for 24 hours at −80° C. After defrosting, the pellet is taken up in the same buffer and then centrifuged. The proteins are quantitatively determined.

Measurements and determination of the Ki The product to be tested is dissolved in DMSO. The membranes (0.8 mg/ml) are incubated at 40° C., 90 min in the presence and in the absence of product and of reference substances. After filtering and washing, the filters are brought into contact with a scintillator and the radioactivity is measured. The Ki is determined using the Graphpad IMPLMOT4 program. The nonspecific is determined with 10$^{-5}$M of GBR 12909.

14) Inhibition of noradrenaline re-uptake Membrane preparation

The membranes are prepared as above. The Tris 50 mM, 300 mM NaCl, 5 nM KCl, pH=7.4 buffer is used in this case.

Measurements and determination of the Ki The procedure followed is identical to that used for the dopamine re-uptake sites. Two incubations are carried out in the presence of antiproteases, one for 360 min at 4° C. and the other for 90 min at 4° C. The non-specific binding is determined with 10$^{-5}$M of Desipramine. The IC$_{50}$ values obtained under these two conditions are identical.

The results are treated as in the preceding test.

15) Inhibition of serotonin re-uptake Membrane preparation

The cortex membranes are prepared as above. The Tris 50 mM, 120 mM NaCl, 5 nM KCl, pH=7.4 buffer is used in this case.

Measurements and determination of the Ki The procedure followed is identical to that used for the dopamine and noradrenaline re-uptake sites.

Incubation is carried out at 22° C. for 1 hour. The non-specific binding is determined with 10$^{-5}$M of Fluoxetine.

The results are treated as in the preceding test.

The specific radioligands, the reference products and the operating conditions used are summarized in Table 5.

RESULTS

The preferred compounds of the invention have a nanomolar affinity with respect to the noradrenaline, dopamine and serotonin re-uptake sites.

We claim:

1. Substituted nitrogenous heterocycle compounds of formula (I)

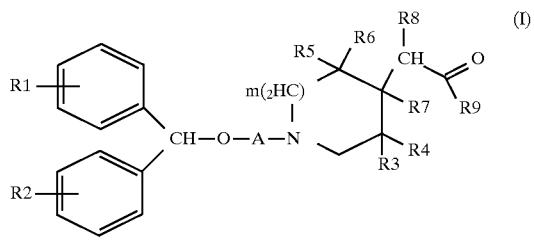

in which:

R$^1$ and R$^2$ which are identical or different, represent a hydrogen atom, a halogen atom, a C$_1$–C$_6$ alkyl group, a C$_1$–C$_6$ alkoxy group or a trifluoromethyl group, m is an integer between 0 and 2, A is a C$_2$–C$_8$ alkylene chain or a C$_2$–C$_8$ alkenylene chain, the heterocyclic unit of general formula Q:

Q = 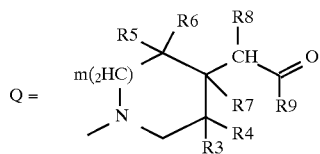

in which

R$^9$ represents a unit —OZ$_1$ in which Z$_1$ represents hydrogen, a C$_1$–C$_{12}$ alkyl, a C$_3$–C$_7$ cycloalkyl, a C$_1$–C$_{12}$ alkyl which is substituted by one or a plurality of optionally esterified alcohol functional groups or a C$_1$–C$_{12}$ alkyl substituted by an —N(RaRb) group in which Ra and Rb, independently of one another, represent hydrogen or a C$_1$–C$_4$ alkyl group or alternatively Ra and Rb, together with the nitrogen atom to which they are bonded, form a 5- to 7-membered heterocycle optionally containing a second heteroatom, a unit —OM in which M is an alkali metal, alkaline earth metal or ammonium cation, a unit —N(Z$_2$Z$_3$) in which Z$_2$ and Z$_3$, independently of one another, represent a hydrogen atom, a C$_1$–C$_{12}$ alkyl, a C$_3$–C$_7$ cycloalkyl, a C$_1$–C$_{12}$ alkyl substituted by an —N(RaRb) group in which Ra and Rb are as defined above or a C$_1$–C$_{12}$ alkyl substituted by one or a plurality of optionally esterified alcohol functional groups or alternatively Z$_2$ and Z$_3$, together with the nitrogen atom to which they are bonded,

TABLE 5

Receptor Study

| SITE | Radioligand | Non-specific | Structure | Reference products | Protein concentration/ml | Time and incubation temperature |
|---|---|---|---|---|---|---|
| Dopamine re-uptake | [$^3$H]-GBR 12935 | 10$^{-5}$M GBR 12909 | Pig striatum | GBR 12909 GBR 12935 | 0.8 mg | 90 minutes at 4° C. |
| Noradrenaline re-uptake | [$^3$H]-Nisoxetine 0.8 nM | 10$^{-5}$M Desipramine | Rat brain | Maprotiline Desipramine | 0.8 mg | 90 minutes at 0° C. |
| Serotonin re-uptake | [$^3$H] Paroxetine 0.12 nM | 10$^{-5}$M Fluoxetine | Rat cortex | Fluoxetine Imipramine | 0.5 mg | 1 hour at 22° C. | form a 5- to 7-membered heterocycle optionally containing a second heteroatom,
represents one of the groups $Q^1$ or $Q^2$ defined below:
$Q^1$ when $R^7$ and $R^8$ are hydrogen atoms,

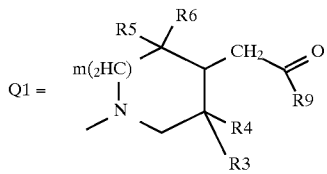

$Q^2$ when $R^7$ and $R^8$ form a double bond,

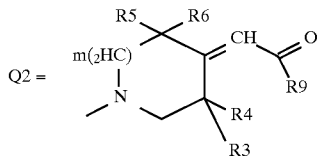

and $R^3$, $R^4$, $R^5$ and $R^6$, are identical or different, represent a hydrogen atom or a $C_1$-$C_8$, alkyl, or alternatively the pairs of radicals $R^3$-$R^4$, $R^5$-$R^6$ and $R^3$-$R^5$ form a 5- to 7-membered ring or heterocycle, provided that:

when m is 1, A is —(CH$_2$)$_2$-, $R^9$ can not be OH, OC$_{1-6}$ alkyl or OM; when m is 1, A is —(CH$_2$)$_3$-, $R^3$, $R^4$, $R^5$ and $R^6$ can not all be hydrogen;

in a racemic or optically pure form and/or in the form of cis/trans isomers, and their pharmaceutically acceptable salts.

2. Substituted nitrogenous heterocycle compounds of claim 1 further provided that:

when $R^1$ and $R^2$ are hydrogen or the methyl group or a chlorine atom and $R^2$ is hydrogen, A is the (CH$_2$)$_2$ group, $R^3$, $R^4$, $R^5$, and $R^6$ are each hydrogen and m is equal to 1, then $R^9$ is not the ethoxy or hydroxyl group, when $R^1$ and $R^2$ are each a fluorine atom in the 4-position, A is the (CH$_2$)$_2$ group, Q is $Q^1$ is which $R^3$, $R^4$, $R^5$, and $R^6$ are each hydrogen and m is equal to 1, then $R^9$ is not the ethoxy group, when A is a C$_2$ alkylene chain and m is equal to 1, at least one of $R^3$, $R^4$, $R^5$ and $R^6$ is not hydrogen or methyl, and when A is a C$_3$-C$_8$ alkylene group and m is equal to 1, at least one of $R^3$, $R^4$, $R^5$ and $R^6$ is not hydrogen, in the racemic or optically pure form and/or in the form of cis/trans isomers, and their pharmaceutically acceptable salts.

3. Compounds according to claim 2, wherein
   $R^1$ and $R^2$, independently of one another, represent a hydrogen or fluorine atom in the 2- or 4-position,
   A is a C$_3$-C$_5$ alkylene chain,
   m is equal to 1,
   Q is $Q^1$
   $R^4$, $R^5$ and $R^6$ represent a hydrogen atom,
   $R^3$ is methyl or ethyl, and
   $R^9$ is ethoxy or hydroxyl.

4. Compounds of the formula (I) according to claim 1, wherein
   $R^1$ and $R^2$, which are identical or different, represent a hydrogen or halogen atom,
   A is an alkylene chain containing 3 to 6 carbon atoms,
   m is an integer equal to 0 or 1, Q represents $Q^1$ as defined in claim 1 in which $R^3$, $R^4$, $R^5$ and $R^6$ represent a hydrogen atom or a methyl group.

5. Compounds of formula (I) according to claim 1 wherein at least one of the $R^3$, $R^4$, $R^5$ and $R^6$ substituents of the heterocycle $Q_1$ is different from the other three, the said derivatives being in the form of cis or trans isomers.

6. Compounds of formula (I) according to claim 1, wherein:
   A is an alkylene chain containing 3 to 6 carbon atoms,
   m is an integer equal to 0 or 1,
   Q represents $Q^2$ in which at least one of the $R^3$, $R^4$, $R^5$ and $R^6$ substituents is different from the other three, the said derivatives being in the form of cis or trans isomers.

7. Compounds of formula (I) according to claim 1, wherein
   $R^1$ and $R^2$ independently represent a hydrogen or a fluorine atom in the 2- or 4-position,
   A is an alkylene chain containing 3 to 5 carbon atoms,
   m is equal to 1,
   Q represents $Q^1$
   $R^4$, $R^5$ and $R^6$ represent a hydrogen atom,
   $R^3$ is a hydrogen or a methyl or ethyl group,
   $R^9$ is an ethoxy or hydroxyl unit.

8. Compounds of formula (I) according to claim 1, wherein:
   $R^1$ and $R^2$, independently of one another, represent a hydrogen or a fluorine atom in the 2- or 4-position,
   A is an alkylene chain containing 3 to 5 carbon atoms,
   m is equal to 1,
   Q represents $Q^1$
   $R^5$ and $R^6$ represent a hydrogen atom,
   $R^3$ and $R^4$, which are identical or different, represent a methyl or ethyl group,
   $R^9$ is an ethoxy or hydroxyl unit.

9. Compounds of formula (I) according to claim 7, wherein:
   $R^1$ and $R^2$, independently of one another, represent a hydrogen or a fluorine atom in the 2- or 4-position,
   A is an alkylene chain containing 3 to 5 carbon atoms,
   m is equal to 1,
   the heterocycle Q represents $Q^1$
   $R^3$, $R^4$, $R^5$ and $R^6$ represent a hydrogen atom,
   $R^9$ is an ethoxy or hydroxyl unit.

10. Compounds according to claim 3, wherein they are chosen from the compounds below:
   ethyl {1-[1-((4,4'-difluorodiphenyl)methoxy)-4-butyl]-3-methyl}piperidino-4-acetate
   ethyl {1-[1-((4,2'-difluorodiphenyl)methoxy)-4-butyl]-3-methyl}piperidino-4-acetate
   ethyl {1-[1-((4,4'-difluorodiphenyl)methoxy)-3-propyl]-3-methyl}piperidino-4-acetate
   ethyl {1-[1-((4,4'-difluorodiphenyl)methoxy)-3-propyl]} piperidino-4-acetate
   ethyl {1-[1-((4,2'-difluorodiphenyl)methoxy)-3-propyl]-3-methyl}piperidino-4-acetate
   ethyl {1-[1-(diphenyl)methoxy)-5-pentyl]-3-methyl}-piperidino-4-acetate
   ethyl {1-[1-(4,4'-difluorodiphenyl)methoxy)-5-pentyl]-3-methyl}piperidino-4-acetate
   ethyl {1-[1-((4-fluorodiphenyl)methoxy)-3-propyl]-3-methyl}piperidino-4-acetate ethyl {1-[1-((4-fluorodiphenyl)methoxy)-4-butyl]-3-methyl}piperidino-4-acetate ethyl {1-[1-((4-fluorodiphenyl)methoxy)-5-pentyl]-3-methyl}piperidino-4-acetate ethyl {1-[4-((4,4'-difluorodiphenyl)methoxy)-4-butyl]-3,3-dimethyl}piperidino-4-acetate {1-[1-((4,4'-difluorodiphenyl)methoxy)-4-butyl]-3-methyl}piperidino-4-acetic acid {1-[1-((4,4'-difluorodiphenyl)methoxy)-4-butyl]-3,3-dimethyl}piperidino-4-acetic acid in the racemic or optically pure form and/or in the form of cis/trans isomers.

11. Compounds of formula (I) according to claim 1, wherein:

Q is $Q^1$ or $Q^2$ as defined in claim 1 in which at least one of the $R^3$, $R^4$, $R^5$ and $R^6$ radicals is other than hydrogen, A is the $(CH_2)_2$ group.

12. Pharmaceutical compositions, containing a therapeutically effective amount of at least one of the substituted nitrogenous heterocycle compounds according to claim 1, in combination with a pharmaceutical vehicle.

13. A method for treatment of humans for depression comprising administering a theraputically amount of a substituted nitrogenous heterocycle compound of formula (I)

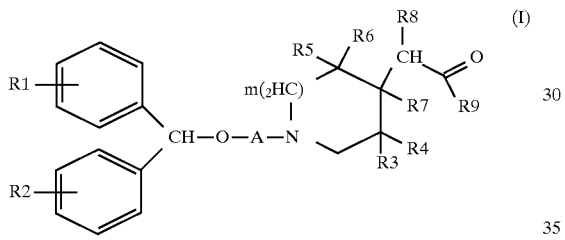

in which:

$R^1$ and $R^2$ which are identical or different, represent a hydrogen atom, a halogen atom, a $C_1$–$C_6$ alkyl group a $C_1$–$C_6$ alkoxy group or a trifluoromethyl group, m is an integer between 0 and 2, A is a $C_2$–$C_8$ alkylene chain or a $C_2$–$C_8$ alkenylene chain, the heterocyclic unit of general formula Q:

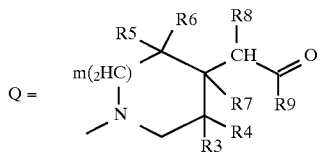

in which $R^9$ represents a unit —$OZ_1$ in which $Z_1$ represents hydrogen, a $C_1$–$C_{12}$ alkyl, a $C_3$–$C_7$ cycloalkyl, a $C_1$–$C_{12}$ alkyl which is substituted by one or a plurality of optionally esterified alcohol functional groups or a $C_1$–$C_{12}$ alkyl substituted by an —N(RaRb) group in which Ra. and Rb, independently of one another, represent hydrogen or a $C_1$–$C_4$ alkyl group or alternatively Ra and Rb, together with the nitrogen atom to which they are bonded, form a 5- to 7-membered heterocycle optionally containing a second heteroatom, a unit —OM in which M is an alkali metal, alkalinre earth metal or ammonium cation, a unit —$N(Z_2Z_3)$ in which $Z_2$ and $Z_3$, independently of one another, represent a hydrogen atom, a $C_1$–$C_{12}$ alkyl, a $C_3$–$C_7$ cycloalkyl, a $C_1$–$C_{12}$ alkyl substituted by an —N(RaRb) group in which Ra and Rb are as defined above or a $C_1$–$C_{12}$ alkyl substituted by one or a plurality of optionally esterified alcohol functional groups or alternatively $Z_2$ and $Z_3$, together with the nitrogen atom to which they are bonded, form a 5- to 7-membered heterocycle optionally containing a second heteroatom, represents one of the groups $Q^1$ or $Q^2$ defined below:

$Q^1$ when $R^7$ and $R^8$ are hydrogen atoms,

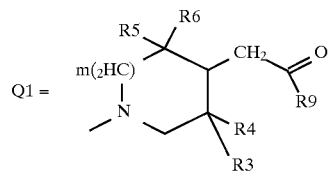

$Q^2$ when $R^7$ and $R^8$ form a double bond,

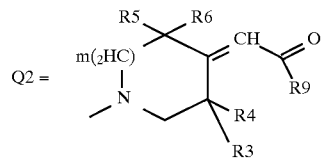

and $R^3$, $R^4$, $R^5$ and $R^6$, are identical or different, and represent a hydrogen atom or a $C_1$–$C_8$ alkyl, or alternatively, the pairs of radicals $R^3$–$R^4$, $R^5$–$R^6$ and $R^3$–$R^5$ form a 5- to 7-membered ring or heterocycle, with the proviso that, when m is 1, A is —$(CH_2)_2$-, $R^9$ can not be OH, $OC_{1-6}$ alkyl or OM; when m is 1, A is —$(CH_2)_3$-, $R^3$, $R^4$, $R^5$ and $R^6$ can not all be hydrogen;

in racemic or optically pure form and/or in the form of cis/trans isomers.

14. A method for treatment of humans for depression comprising administering a therapeutically effective amount of a substituted nitrogenous heterocycle compound of claim 1 further provided that when A is a $C_2$ alkylene chain and m is equal to 1, at least one of $R^3$, $R^4$, $R^5$ and $R^6$ is not hydrogen or methyl, and when A is a $C_3$–$C_8$ alkylene group and m is equal to 1, at least one of $R^3$, $R^4$, $R^5$ and $R^6$ is not hydrogen, in racemic or optically pure form and/or in the form of cis/trans isomers.

* * * * *